United States Patent
Koishi

(10) Patent No.: US 9,072,440 B2
(45) Date of Patent: Jul. 7, 2015

(54) RADIOGRAPHIC SYSTEM AND CONTROL METHOD THEREOF

(71) Applicant: FUJIFILM Corporation, Tokyo (JP)

(72) Inventor: Takeshi Koishi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 256 days.

(21) Appl. No.: 13/732,867

(22) Filed: Jan. 2, 2013

(65) Prior Publication Data

US 2013/0208852 A1 Aug. 15, 2013

(30) Foreign Application Priority Data

Feb. 10, 2012 (JP) ................... 2012-027037

(51) Int. Cl.
| | |
|---|---|
| *A61B 6/08* | (2006.01) |
| *A61B 6/03* | (2006.01) |
| *A61B 6/00* | (2006.01) |
| *A61B 6/02* | (2006.01) |

(52) U.S. Cl.
CPC .............. *A61B 6/032* (2013.01); *A61B 6/548* (2013.01); *A61B 6/025* (2013.01); *A61B 6/4233* (2013.01); *A61B 6/4283* (2013.01); *A61B 6/5288* (2013.01); *A61B 6/542* (2013.01)

(58) Field of Classification Search
USPC .............. 378/21, 22, 24, 25, 26, 27; 382/131, 382/132
See application file for complete search history.

(56) References Cited

U.S. PATENT DOCUMENTS

| | | | |
|---|---|---|---|
| 5,680,430 A | 10/1997 | Khutoryansky et al. | |
| 2007/0025502 A1* | 2/2007 | Bessho | .......... 378/19 |
| 2008/0247509 A1 | 10/2008 | Kashiwagi | |

FOREIGN PATENT DOCUMENTS

| | | |
|---|---|---|
| JP | H03-121056 A | 5/1991 |
| JP | H06-154194 A | 6/1994 |
| JP | H10-327317 A | 12/1998 |
| JP | 2000-501552 A | 2/2000 |
| JP | 2007-089783 A | 4/2007 |
| JP | 2008-253555 A | 10/2008 |

OTHER PUBLICATIONS

The Notice of Reasons for Rejection issued in Japanese Application No. 2012-027037 on Jan. 22, 2014.

* cited by examiner

*Primary Examiner* — Nicole Ippolito
(74) *Attorney, Agent, or Firm* — Birch, Stewart, Kolasch & Birch, LLP

(57) ABSTRACT

A detection field setting unit of a console sets a detection field of detection pixels of an electronic cassette which are used to detect the dose of X-rays passing through a subject so as to correspond to each irradiation position on the basis of irradiation positions of an X-ray source set by a driving condition setting unit and ROI information such as the position and the size of a region of interest (ROI) of the subject M input through an input device and the height thereof from a radiography platform. The electronic cassette performs an automatic exposure control of detecting the dose of X-rays by the use of the detection pixels in the detection field set by the detection field setting unit of the console and automatically controlling the irradiation dose of X-rays on the basis of the detected dose, when performing a radiographing operation at the irradiation positions.

20 Claims, 20 Drawing Sheets

FIG. 6

| RADIOGRAPHING SITE | TUBE VOLTAGE (kV) | IRRADIATION STOP THRESHOLD |
|---|---|---|
| ⋮ | ⋮ | ⋮ |
| CHEST | V1 | th1 |
| HEAD | V2 | th2 |
| ⋮ | ⋮ | ⋮ |

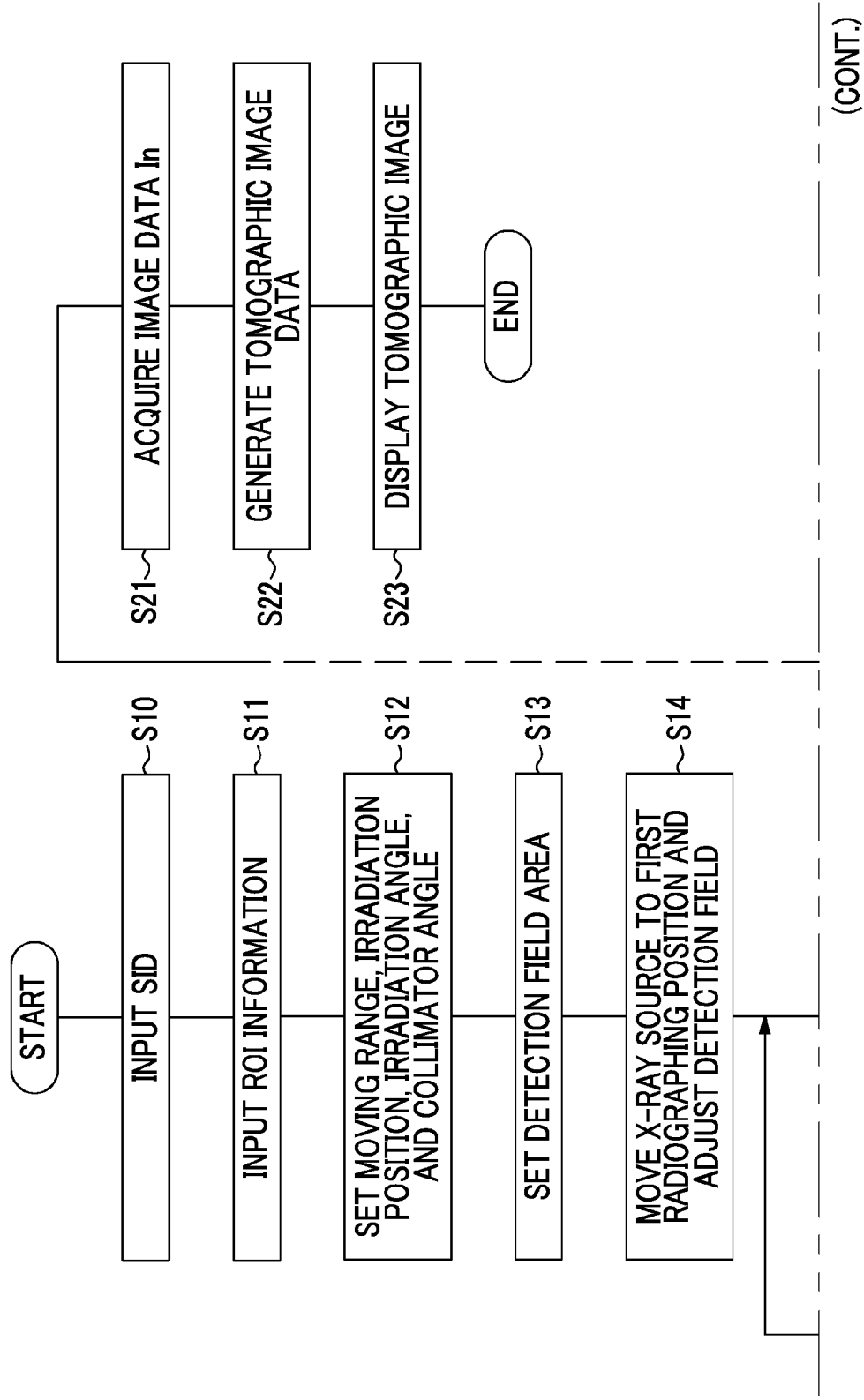

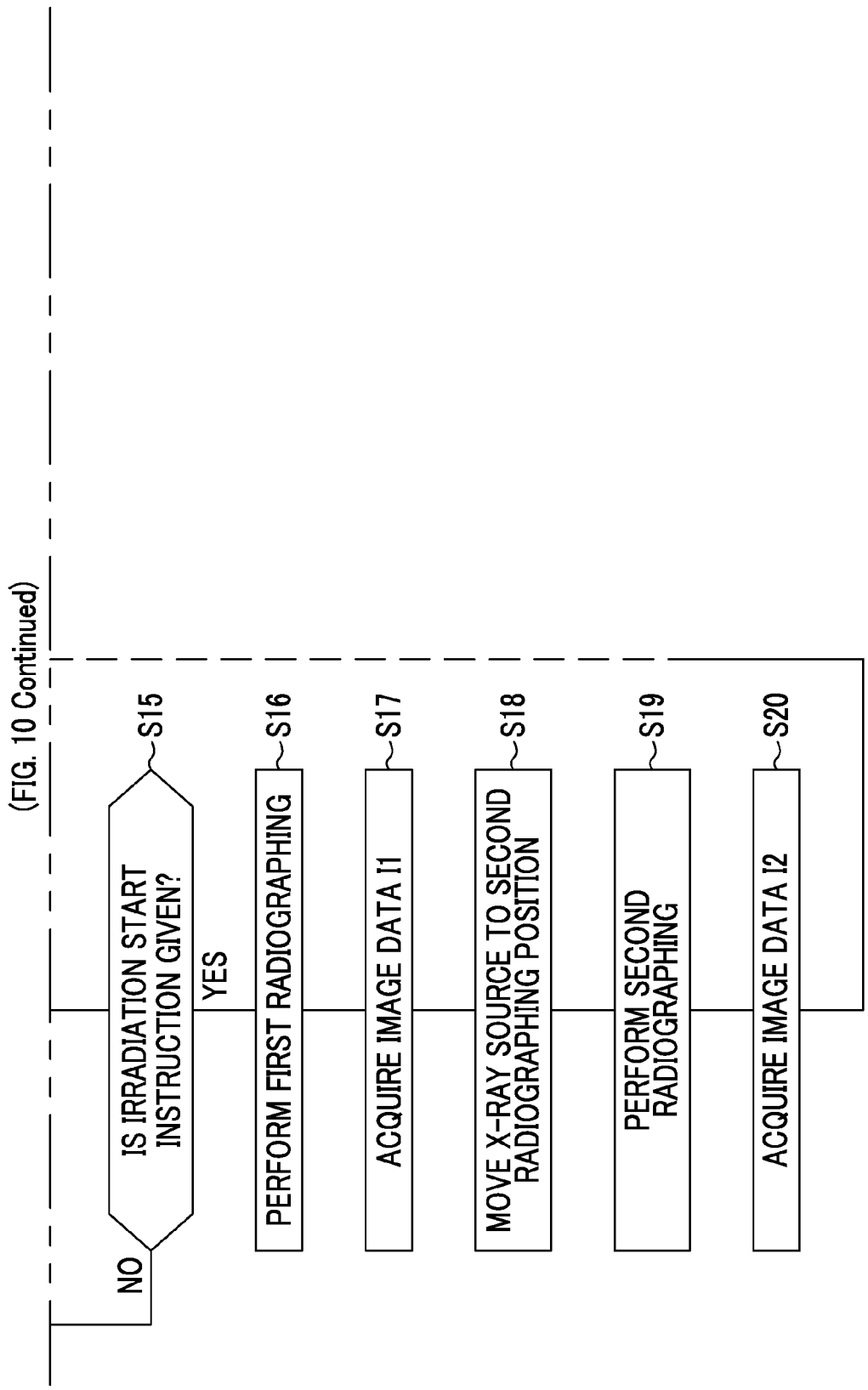

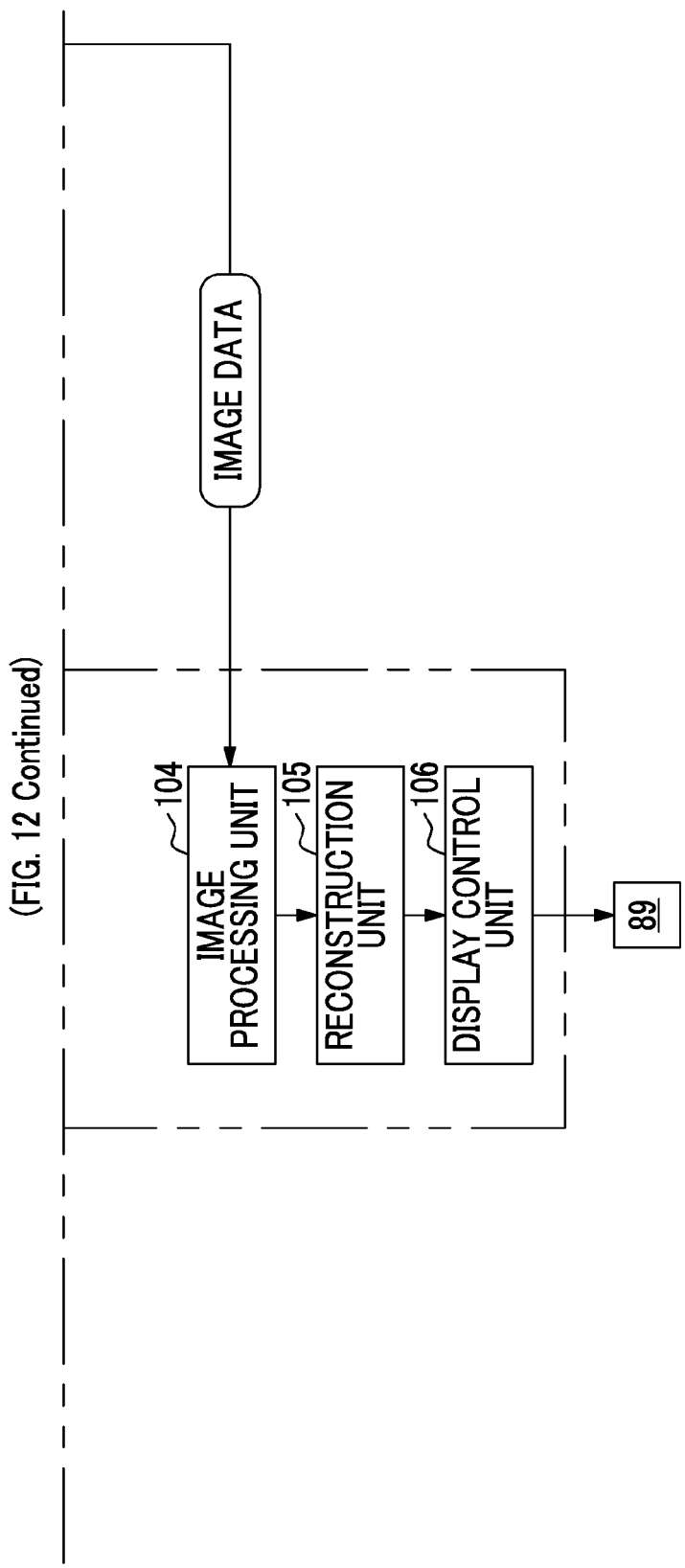

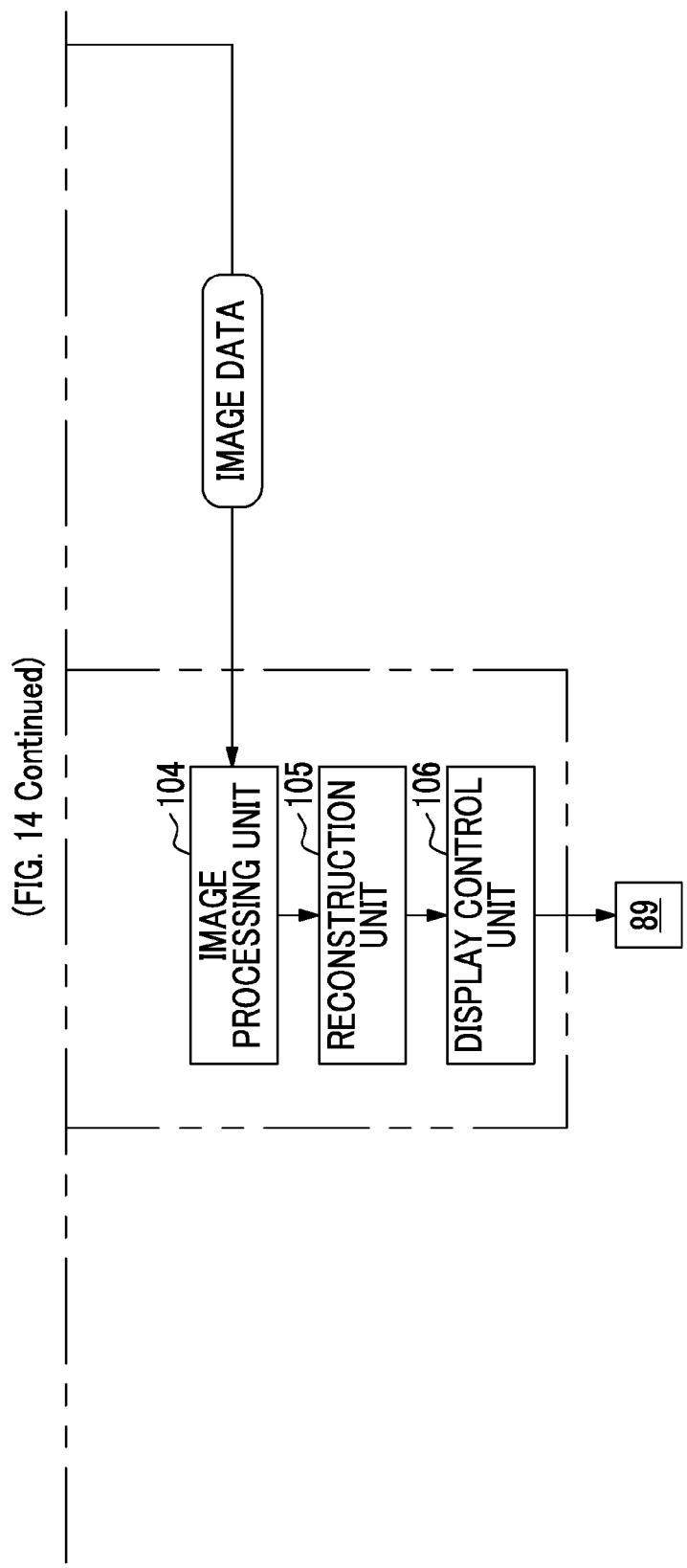

RADIOGRAPHIC SYSTEM AND CONTROL METHOD THEREOF

BACKGROUND OF THE INVENTION

1. Field of the Invention

The present invention relates to a radiographic system that radiographs a tomographic image using radiation and a control method of the radiographic system.

2. Description of the Related Art

In the medical fields, radiographic systems using radiation such as X-rays are known. A radiographic system includes an X-ray generator including an X-ray source generating X-rays and an X-ray imaging apparatus receiving X-rays and capturing an X-ray image. As an X-ray imaging apparatus, an X-ray image detector using as a detection panel a flat panel detector (FPD) in which pixels accumulating signal charges corresponding to the dose of X-rays are arranged in a matrix shape has been widely spread. The FPD accumulates signal charges in the respective pixels and converts the accumulated signal charges into a voltage signal through the use of a signal processing circuit, whereby an X-ray image representing image information of the subject is detected and is output as digital image data.

A radiographic system is known which detects the dose of X-rays passing through a subject through the use of a dose sensor and performs an automatic exposure control (AEC) of stopping irradiation with X-rays from an X-ray generator when the integrated value of the doses reach a predetermined threshold. In a radiographic system including plural dose detectors, a detection field corresponding to a region (also referred to as "a region of interest (ROI)") to which attention should be most paid is set for each radiographing site and the irradiation stop of X-rays is determined on the basis of the X-ray dose from the dose sensors in the detection field.

A radiographic system is also known which performs a tomosynthesis imaging of causing an X-ray source to move and irradiate a subject with X-rays from different irradiation angles to perform plural radiographing operations and reconstructing plural images acquired through the radiographing operations to generate a tomographic image in which a desired tomographic plane is emphasized. In the tomosynthesis imaging, the distance traversed by X-rays passing through a subject, that is, the thickness of the subject, varies depending on the irradiation angle of X-rays. Accordingly, when the tomosynthesis imaging is performed with a fixed dose, the density of the detection field of each image differs. Therefore, in radiographic systems described in JP2000-501552T and JP2008-253555A, the variation in thickness of a subject is predicted on the basis of the irradiation angle of X-rays and the subject is irradiated with X-rays of the dose corresponding to the predicted thickness of the subject.

SUMMARY OF THE INVENTION

In the radiographic systems described in JP2000-501552T and JP2008-253555A, the variation in thickness of a subject is predicted on the basis of the irradiation angle of X-rays. However, the variation in thickness of a subject differs depending on radiographing sites, and sites in which the thickness greatly varies with a slight difference of the irradiation angle or sites in which the thickness hardly varies with a slight difference of the irradiation angle exist. Accordingly, the tomosynthesis imaging of changing the dose of X-rays on the basis of the irradiation angle of X-rays has poor stability, from the viewpoint of making the densities of detection fields of respective images uniform.

The present invention has been made in view of the above-mentioned problems and an object of the present invention is to provide the densities of detection fields of a series of images acquired through a tomosynthesis imaging uniform.

According to an aspect of the present invention, there is provided a radiographic system including: a radiation source that irradiates a subject with radiation from different directions at plural irradiation positions; a radiological image detector that includes a detection panel in which plural pixels receiving radiation passing through the subject are arranged and that receives the radiation radiated from plural irradiation directions from the radiation source and detects a series of radiological images; plural dose sensors that are arranged on an imaging plane on which the pixels of the detection panel are formed and that detect the dose of radiation passing through the subject; a detection field setting unit that sets a detection field of the dose sensors, which is used to detect the dose of radiation passing through the subject, depending on the irradiation positions of the radiation source; a density adjusting unit that adjusts the densities of the detection fields of the series of radiological images on the basis of the dose detected by the dose sensors in the detection field; and a tomographic image generating unit that generates a tomographic image of the subject from the series of radiological images.

The detection field setting unit may set the detection field on the basis of the position and size of a region of interest of the subject and the movement position of the radiation source. In this case, the radiographic system may further include a region of interest setting unit that sets the position and size of a region of interest of the subject.

The detection field setting unit may calculate a distance X1 from the radiation source to an edge of the detection field close to the radiation source and a distance X2 from the radiation source to an edge of the detection field distant from the radiation source through the use of the following expressions (1) and (2):

$$X1 = SID/(SID-H_{ROI}) \times (L_{XRAI} - L_{ROI}/2) \quad (1)$$

$$X2 = SID/(SID-H_{ROI}) \times (L_{XRAI} + L_{ROI}/2) \quad (2)$$

where $L_{ROI}$ represents the size of the region of interest in the moving direction of the radiation source, SID represents the distance between the detection panel and the radiation source in the direction perpendicular to the imaging plane of the detection panel, $L_{XRAI}$ represents position information of the moving direction of the radiation source with respect to the central axis of the region of interest in the direction perpendicular to the imaging plane of the detection panel, and $H_{ROI}$ represents the distance from the imaging plane of the detection panel to the region of interest.

The detection field setting unit may set the detection field on the basis of an irradiation field of the radiation radiated from the radiation source and the movement position of the radiation source. In this case, the radiation source may further include an irradiation field limiter that sets the irradiation field.

The detection field setting unit may calculate a distance X1a from the radiation source to an edge of the detection field close to the radiation source and a distance X2a from the radiation source to an edge of the detection field distant from the radiation source through the use of the following expressions (3) and (4):

$$X1a = SID \cdot \tan(\theta 1 - \theta 2/2) \quad (3)$$

$$X2a = SID \cdot \tan(\theta 1 + \theta 2/2) \quad (4)$$

where L1 represents position information of the moving direction of the radiation source with respect to the central position of the imaging plane of the detection panel, θ1 represents the irradiation angle of radiation with respect to the imaging plane of the detection panel, and θ2 represents the opening angle of the irradiation field limiter.

The detection field setting unit may specify a region of interest of the subject from a firstly-detected radiological image out of the series of radiological images detected by the radiological image detector and may set the detection field to be used to detect the second or subsequent radiological image on the basis of the detection field corresponding to the region of interest and the movement position of the radiation source.

The density adjusting unit may compare the integrated value of the doses detected by the dose sensors in the detection field with a predetermined irradiation stop threshold and may perform an automatic exposure control of stopping the irradiation with radiation from the radiation source when the integrated value reaches the irradiation stop threshold.

Another density adjusting unit may be used. In this case, the density adjusting unit may adjust a gain of image data of the radiological image on the basis of the integrated value of the doses detected by the dose sensors in the detection field when reading the image data from the detection panel. When the gain is adjusted by the use of the density adjusting unit, the density adjusting unit may normalize the series of radiological images of which the gain is adjusted by multiplying the radiological images by the reciprocal of the gain.

According to another aspect of the present invention, there is provided a control method of a radiographic system including: setting a detection field, which is used to detect the dose of radiation passing through a subject, from a plurality of dose sensors arranged on an imaging plane on which pixels of a detection panel are formed depending on the irradiation position of a radiation source; adjusting the densities of the detection fields of the series of radiological images on the basis of the dose detected by the dose sensors in the detection field; and generating a tomographic image of the subject from the series of radiological images.

According to the present invention, since the AEC is performed for each radiographing operation of the tomosynthesis imaging, it is possible to improve the balance of the densities of the detection fields of a series of radiological images acquired for each radiographing and thus to acquire a tomographic image with high image quality. Since the AEC of each radiographing uses the detection field set depending on the irradiation position of the radiation source, it is possible to perform a radiographing operation with appropriate densities of the detection fields of a series of radiological images. Since the detection field is automatically set on the basis of the irradiation position of the radiation source, it is possible to simply and rapidly set the detection field.

BRIEF DESCRIPTION OF THE DRAWINGS

FIG. 6 is a diagram illustrating radiographing conditions set in a console.

FIG. 10 is a flowchart illustrating the flow of processes of a tomosynthesis imaging.

DESCRIPTION OF THE PREFERRED EMBODIMENTS

Figure 1:
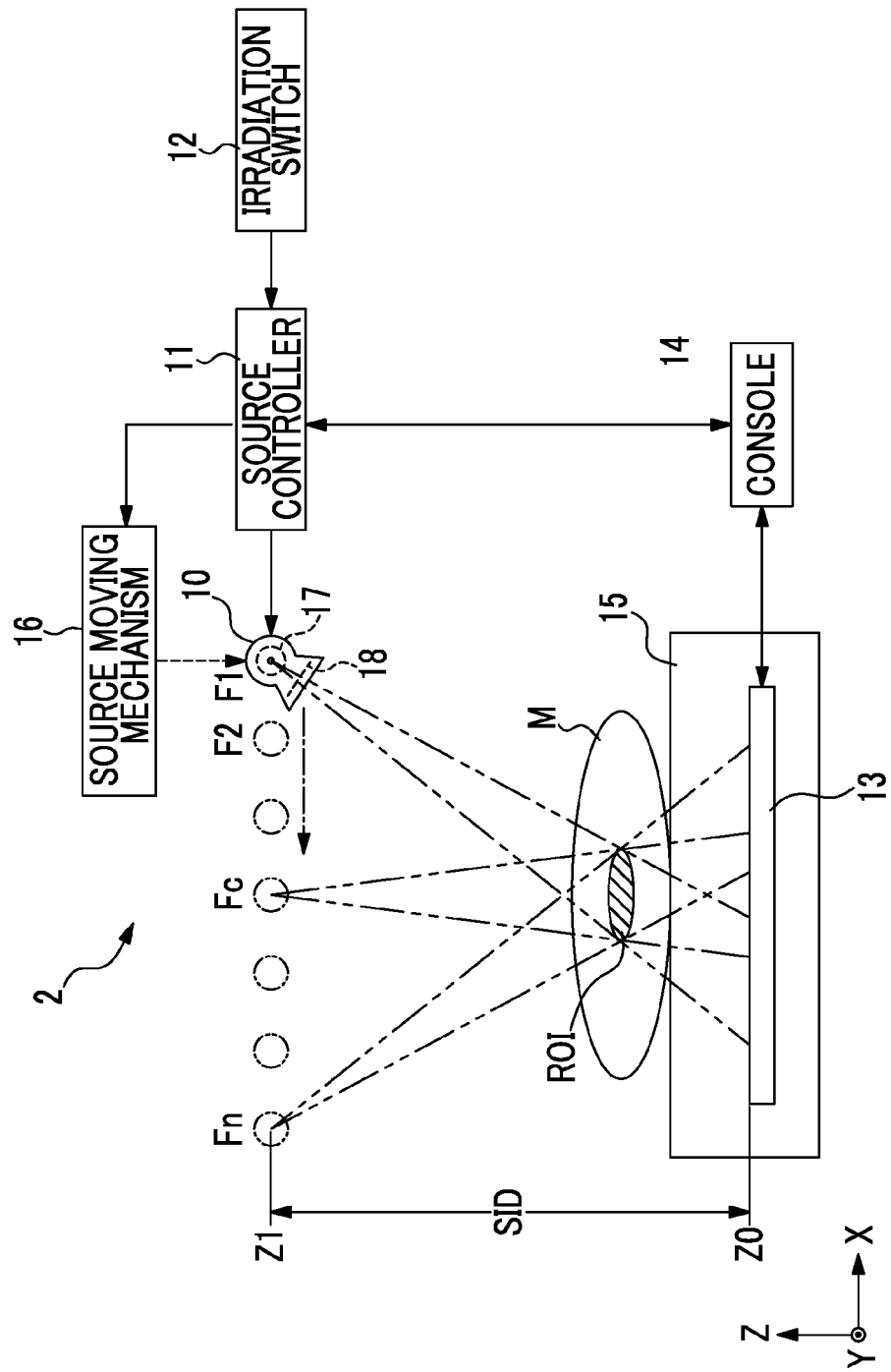
FIG. 1 is a diagram schematically illustrating the configuration of a radiographic system.

In FIG. 1, a radiographic system 2 includes an X-ray source 10, a radiography platform 15 that is disposed to face the X-ray source 10 and on which a subject M is placed, an electronic cassette 13 that detects X-rays passing through the subject M and outputs an X-ray image, a source moving mechanism 16 that causes the X-ray source 10 to move to plural predetermined positions, a source controller 11 that controls the X-ray source 10 to irradiate the subject M on the electronic cassette 13 with X-rays when the X-ray source 10 reaches a predetermined position (hereinafter, referred to as an irradiation position), and a console 14 that controls the electronic cassette 13 and that reconstructs a series of X-ray images sequentially transmitted from the electronic cassette 13 to generate a tomographic image. A tomographic image generating unit constitutes a part of the console 14 and a radiological image detector constitutes a part of the electronic cassette 13.

The radiographic system 2 performs a tomosynthesis imaging operation of acquiring plural X-ray images from the electronic cassette 13 and reconstructing this series of X-ray images by the use of the console 14 to acquire a tomographic image of a subject M by irradiating the subject M on the electronic cassette 13 with X-rays from different directions from the X-ray source 10 at plural irradiation positions while moving the X-ray source 10 disposed to oppose the electronic cassette 13 to plural positions. FIG. 1 shows an example where the X-ray source 10 is made to move along a straight trajectory in the X direction parallel to a detection plane of the electronic cassette 13 by the source moving mechanism 16 in a state where the electronic cassette 13 is fixed, but the X-ray source 10 and the electronic cassette 13 may be made to relatively move in the opposite directions in synchronization with each other with the subject M interposed therebetween.

The radiographing of the radiographic system 2 has a concept of individual radiographing operations performed when the X-ray source 10 reaches plural predetermined positions and a concept of considering the overall individual radiographing operations as a single radiographing operation. Therefore, the individual radiographing operations are referred to as "X-ray imaging" and the radiographing operation in which the overall individual radiographing operations is considered as a single radiographing operation is referred to as "tomosynthesis imaging".

The X-ray source 10 includes an X-ray tube 17 radiating X-rays and an irradiation field limiter (collimator) 18 limiting the irradiation field of X-rays radiated from the X-ray tube 17 to a rectangular shape. The X-ray tube 17 includes a negative electrode formed of a filament emitting thermal electrons and a positive electrode (target) with which the thermal electrons radiated from the negative electrode collide to radiate X-rays. The irradiation field limiter 18 includes plural lead strips blocking X-rays, which are arranged in a parallel-crosses shape and in which an irradiation aperture transmitting X-rays is formed at the center thereof, and moves the positions of the lead strips to change the size of the irradiation aperture and to limit the irradiation field under the control of the source controller 11.

In the tomosynthesis imaging, the source controller 11 controls the driving of the source moving mechanism 16 so as to irradiate the subject M with X-rays at irradiation angles, which correspond to the irradiation positions, from the plural irradiation positions F1 and F2 to Fn set in the moving path by rotating the X-ray source 10 about the axis in the Y direction while moving the X-ray source 10 in the X direction parallel to the imaging plane of the electronic cassette 13. The source moving mechanism 16 includes an arm that is vertically suspended from the ceiling, a holding unit that holds the X-ray source 10 with the tip of the arm and that causes the X-ray source to oscillate about the axis in the Y direction, rails that allow the X-ray source 10 to move in the X and Y directions with respect to the arm, and a drive source such as a motor that drives these units, and can change the position of the X-ray source 10 automatically or manually by an operator such as a radiographer under the control of the source controller 11.

Figure 2:
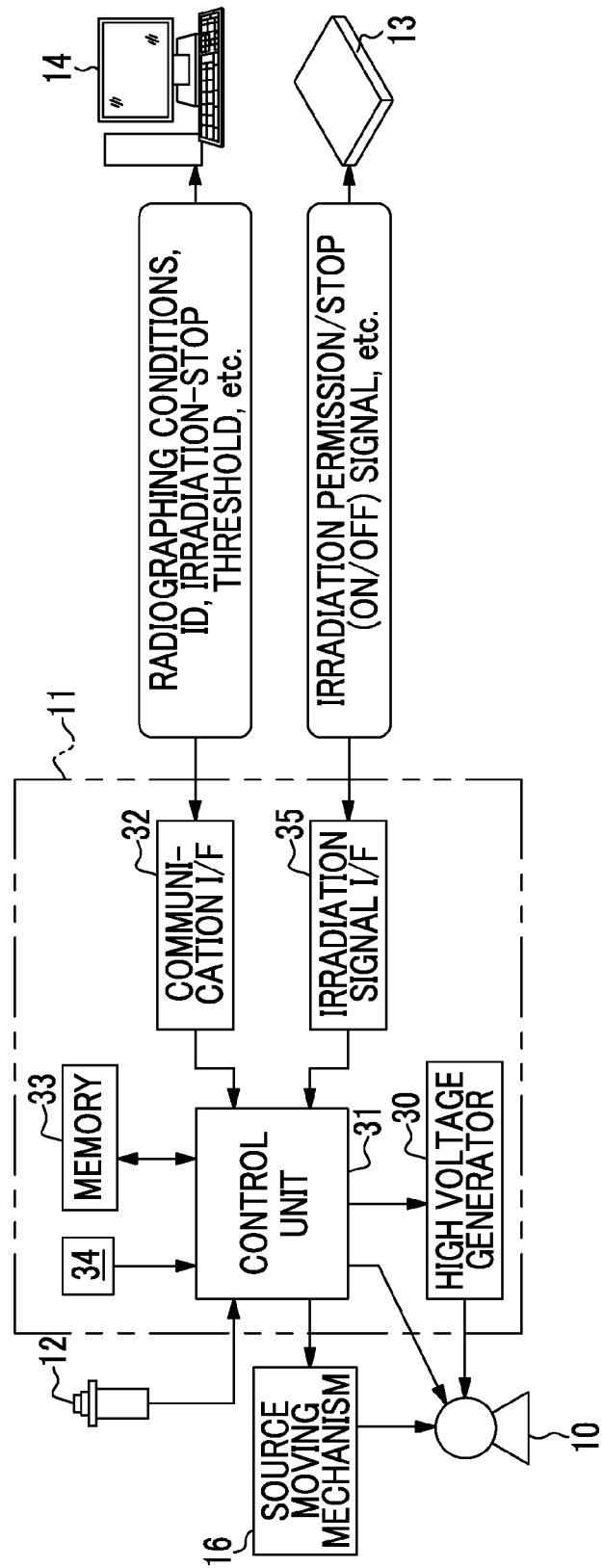
FIG. 2 is a diagram illustrating the internal constitution of a source controller and connections between the source controller and other devices.

As shown in FIG. 2, the source controller 11 includes a high voltage generator 30 that raises an input voltage through the use of a transformer to generate a high tube voltage and that supplies the generated high tube voltage to the X-ray source 10 via a high-voltage cable, a control unit 31 that controls the tube voltage for determining an energy spectrum of X-rays radiated from the X-ray source 10, the tube current for determining an irradiation dose per unit time, and the irradiation time of X-rays, and a communication I/F 32 that relays important information and transmission and reception of signals with the console 14.

An irradiation switch 12, a memory 33, and a touch panel 34 are connected to the control unit 31. The irradiation switch 12 is, for example, a two-step push switch manipulated by an operator, generates a warm-up start signal for starting warming-up of the X-ray source 10 by the first-step push, and generates an irradiation start signal for starting the irradiation from the X-ray source 10 by the second-step push. These signals are input to the source controller 11 via a signal cable. The control unit 31 starts the supply of power from the high voltage generator 30 to the X-ray source 10, when receiving the irradiation start signal from the irradiation switch 12.

The memory 33 stores plural types of radiographing conditions such as a tube voltage and a tube current-irradiation time product (value in mAs) in advance. The radiographing conditions are manually set by an operator through the use of the touch panel 34. The source controller 11 emits X-rays with the tube voltage or the tube current-irradiation time product of the set radiographing conditions. The AEC serves to stop the irradiation with X-rays when it is detected that a necessary and sufficient dose is reached, even when the tube current-irradiation time product (irradiation time) is lower than or equal to the tube current-irradiation time product with which the source controller 11 is expected to radiate X-rays. In order to prevent the lack of dose due to the end of the irradiation with X-rays before a target dose is reached and the irradiation stop is determined by the AEC, the maximum value of the tube current-irradiation time product (irradiation time) is set as the radiographing conditions of the X-ray source 10.

The irradiation signal I/F 35 is connected to the electronic cassette 13 when the irradiation stop time of X-rays is defined on the basis of the output of the detection pixels 65 (see FIG. 3) of the electronic cassette 13. In this case, the control unit 31 transmits an inquiry signal to the electronic cassette 13 via the irradiation signal I/F 35 when receiving the warm-up start signal from the irradiation switch 12. When receiving the inquiry signal, the electronic cassette 13 ends a reset process or performs a preliminary process such as an accumulation starting process. When an irradiation permission signal as a response to the inquiry signal is received from the electronic cassette 13 via the irradiation signal I/F 35 and the irradiation start signal is received from the irradiation switch 12, the control unit 31 starts the supply of power to the X-ray source 10 from the high voltage generator 30. When receiving the irradiation stop signal transmitted from the electronic cassette 13 via the irradiation signal I/F 35, the control unit 31 stops the supply of power from the high voltage generator 30 to the X-ray source 10 and stops the irradiation of X-rays.

The electronic cassette 13 includes an FPD 40 as widely known and a portable chassis (not shown) receiving the FPD 40. The chassis of the electronic cassette 13 has approximately a flat rectangular shape and the two-dimensional size thereof is the same size (the size based on the international standard ISO 4090; 2001) as a film cassette or an IP cassette (also referred to as a CR cassette). Accordingly, the electronic cassette can be mounted on an existing radiography platform for the film cassette or the IP cassette.

The electronic cassette 13 is detachably set into the radiography platform 15 so that the imaging plane 41 of the FPD 40 is maintained with a posture opposing the X-ray source 10. The electronic cassettes 13 may be used as a unified body by placing the electronic cassette on a bed on which a subject M lies or causing a subject M to carry the electronic cassette, instead of setting the electronic cassette on the radiography platform 15.

Figure 3:
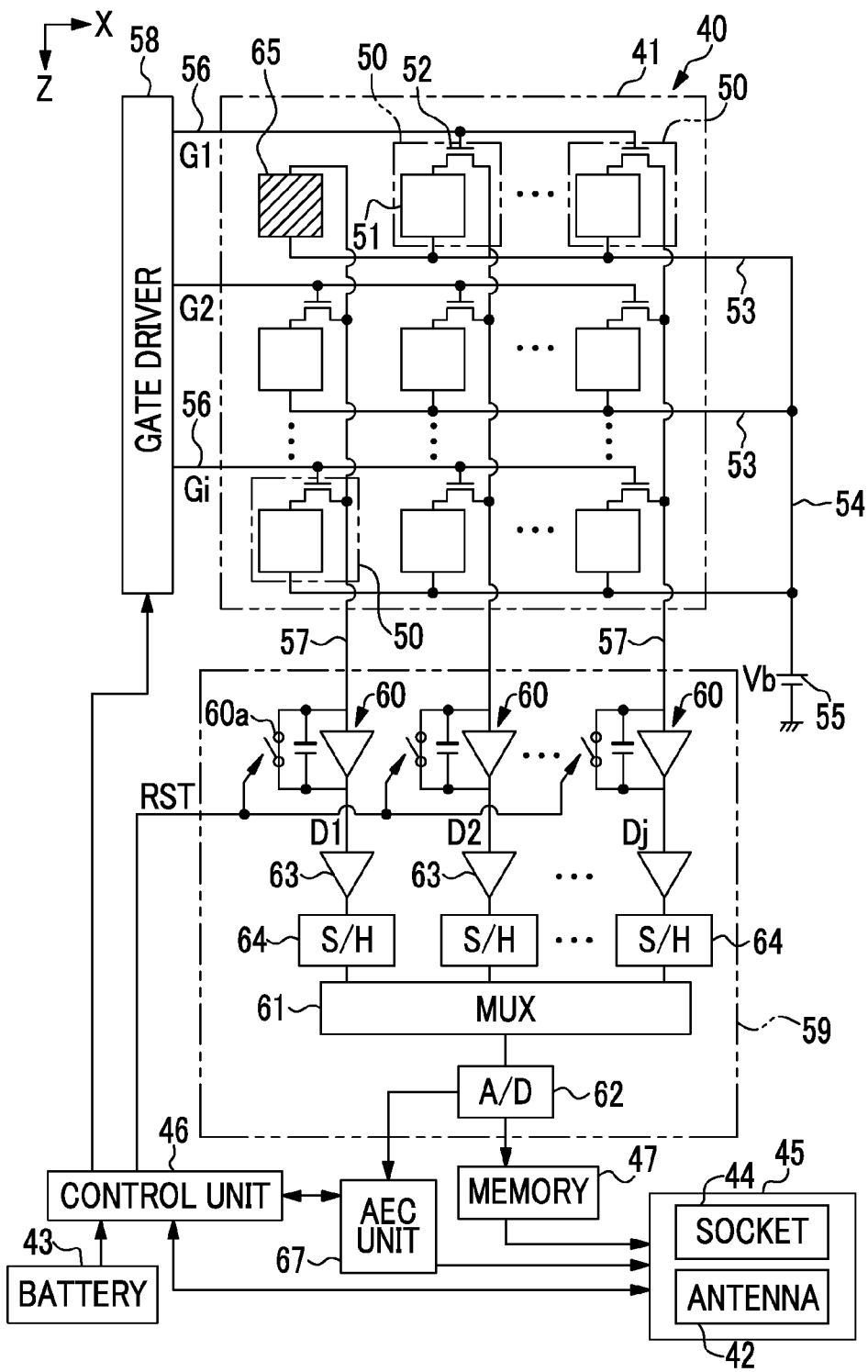
FIG. 3 is a block diagram illustrating the internal constitution of an electronic cassette.

As shown in FIG. 3, the electronic cassette 13 has an antenna 42 and a battery 43 built therein and can wirelessly communicate with the console 14. The antenna 42 transmits and receives electric waves for wireless communication to and from the console 14. The battery 43 supplies power for operating the constituents of the electronic cassette 13. Regarding the battery 43, a small battery is used so as to be received in the thin electronic cassette 13. The battery 43 may be taken out of the electronic cassette 13, may be set in a dedicated cradle, and may be charged. The battery 43 may be configured to be suppliable with power in a wireless manner.

The electronic cassette 13 is provided with a socket 44 in addition to the antenna 42. The socket 44 is disposed for wired connection to the console 14 and is used when the wireless communication between the electronic cassette 13 and the console 14 is not possible due to a lack of capacity of the battery 43 or the like. When a cable from the console 14 is connected to the socket 44, the wired communication with the console 14 becomes possible. At this time, power may be supplied from the console 14 to the electronic cassette 13.

The antenna 42 and the socket 44 are disposed in the communication unit 45. The communication unit 45 relays transmission and reception of a variety of information including image data or signals (such as a life check signal for inspecting whether communication is normally performed) between the antenna 42 or the socket 44 and the control unit 46 or the memory 47.

The FPD 40 (dose sensor) has a TFT active matrix substrate and also includes an imaging plane 41 in which plural pixels 50 accumulating signal charges corresponding to the incident dose of X-rays are arranged on the substrate. The plural pixels 50 are two-dimensionally arranged in a matrix shape of i rows (X direction)×j columns (Z direction) at predetermined pitches.

The FPD 40 further includes a scintillator (fluorescent substance, not shown) converting X-rays into visible rays and is of an indirect conversion type photoelectrically converting the visible rays converted by the scintillator by the use of the pixels 50. The scintillator is formed of CsI (cesium iodide), GOS (gadolinium oxysulfide), or the like, and is disposed to oppose the front surface of the imaging plane 41 on which the pixels 50 are arranged. The scintillator and the FPD 40 may be a PSS (Penetration Side Sampling) type in which the scintillator and the FPD 40 are arranged in this order when seen from the incidence side of X-rays, or may be an ISS (Irradiation Side Sampling) type in which the FPD 40 and the scintillator are arranged in this order to the contrary. A direct conversion type FPD employing a conversion layer (amorphous selenium) directly converting X-rays into charges instead of the scintillator may be used.

Each pixel 50 includes a photodiode 51 which is a photoelectric conversion element generating charges (electron-hole pairs) in response to the incidence of visible rays, a capacitor (not shown) accumulating the charges generated from the photodiode 51, and a thin film transistor (TFT) 52 as a switching element.

The photodiode 51 has a structure in which a semiconductor layer (for example, PIN type) generating charges and an upper electrode and a lower electrode disposed on and under the semiconductor layer are arranged. In the photodiode 51, the TFT 52 is connected to the lower electrode and a bias line 53 is connected to the upper electrode. The bias lines 53 corresponding to the number of rows (i rows) of the pixels 50 in the imaging plane 41 are disposed and are connected to a connection line 54. The connection line 54 is connected to a bias power source 55. A bias voltage Vb is applied from the bias power source 55 to the upper electrode of the photodiode 51 via the connection line 54 and the bias line 53. An electric field is generated in the semiconductor layer with the application of the bias voltage Vb, charges (electron-hole pairs) generated in the semiconductor layer through the photoelectric conversion move to the upper electrode and the lower electrode of which one has a plus polarity and the other has a minus polarity, and the charges are accumulated in the capacitor.

In the TFT 52, the gate electrode is connected to a scanning line 56, the source electrode is connected to a signal line 57, and the drain electrode is connected to the photodiode 51. The scanning lines 56 and the signal lines 57 are wired in a lattice shape, the number of scanning lines 56 corresponds to the number of rows (i rows) of the pixels 50 in the imaging plane 41, and the number of signal lines 57 corresponds to the number of columns (j columns) of the pixels 50. The scanning lines 56 are connected to a gate driver 58 and the signal lines 57 are connected to a signal processing circuit 59.

The gate driver 58 drives the TFT 52 to perform an accumulating operation of accumulating signal charges corresponding to the incident dose of X-rays in the pixels 50 and to perform a reading (main reading) operation and a reset (idle reading) operation of reading the signal charges from the pixels 50. The control unit 46 controls the start times of the operations performed by the gate driver 58.

In the accumulating operation, the TFTs 52 are turned off and the signal charges are accumulated in the pixels 50 in the meantime. In the reading operation, gate pulses G1 to Gi driving the TFTs 52 in the same row at a time are sequentially generated from the gate driver 58 to sequentially activate the scanning lines 56 row by row and the TFTs 52 connected to the scanning lines 56 are turned on row by row. The charges accumulated in the capacitors of the pixels 50 are read to the signal lines 57 when the corresponding TFTs 52 are turned on, and are input to the signal processing circuit 59.

Dark charges are generated in the semiconductor layer of the photodiode 51 regardless of the incidence of X-rays. Since the bias voltage Vb is applied, the dark charges are accumulated in the corresponding capacitor. Since the dark charged generated in the pixels 50 serve as noise components in image data, a reset operation is performed to remove the dark charges. The reset operation is an operation of sweeping out the dark charges generated in the pixels 50 through the use of the signal lines 57.

The reset operation is performed, for example, in a sequential reset type of resetting the pixels 50 row by row. In the sequential reset type, similarly to the operation of reading the signal charges, gate pulses G1 to Gi are sequentially generated from the gate driver 58 to the scanning lines 56 to turn on the TFTs 52 of the pixels 50 row by row. When the TFT 52 is turned on, the dark charges flow from the corresponding pixel 50 to an integration amplifier 60 via the corresponding signal line 57. In the reset operation, unlike the reading operation, the reading of the charges accumulated in the integration amplifiers 60 by a multiplexer (MUX) 61 is not performed and a reset pulse RST is output from the control unit 46 in synchronization with the generation of the gate pulses G1 to Gi to reset the integration amplifiers 60.

Instead of the sequential reset type, a parallel reset type of sequentially resetting groups, each of which include plural rows of pixels, and simultaneously sweeping out the dark charges of the rows in the corresponding group or an overall pixel reset type of giving a gate pulse to the overall rows and simultaneously sweeping out the dark charges of all the pixels may be used. It is possible to raise the speed of the reset operation by using the parallel reset type or the overall pixel reset type.

The signal processing circuit 59 includes integration amplifiers 60, a MUX 61, and an A/D converter 62. The integration amplifiers 60 are individually connected to the signal lines 57. Each integration amplifier 60 includes an operational amplifier and a capacitor connected between input and output terminals of the operational amplifier. The signal line 57 is connected to one input terminal of the operational amplifier. The other input terminal of the integration amplifier 60 is connected to the ground (GND). The integration amplifiers 60 integrate the charges input from the signal lines 57, convert the integrated charges into voltage signals D1 to Dj, and output the voltage signals. The MUX 61 is connected to the output terminal of the integration amplifier 60 of each column via amplifiers 63, sampling and holding (S/H) units 64. The A/D converter 62 is connected to the output side of the MUX 61.

The MUX 61 sequentially selects one integration amplifier 60 from the plural integration amplifiers 60 connected in parallel and serially inputs the voltage signals D1 to Dj output from the selected integration amplifier 60 to the A/D converter 62. The A/D converter 62 converts the input voltage signals D1 to Dj to digital data and outputs the digital data to the memory 47 built in the electronic cassette 13. An amplifier may be connected between the MUX 61 and the A/D converter 62.

When the voltage signals D1 to Dj corresponding to one row are read from the integration amplifiers 60 by the MUX 61, the control unit 46 outputs a reset pulse RST to the integration amplifiers 60 and turns on a reset switch 60a of the integration amplifier 60. Accordingly, the signal charges of one row accumulated in the integration amplifiers 60 are reset. When the integration amplifiers 60 are reset, the gate pulse of the next row is output from the gate driver 58 and the reading of signal charges in the pixels 50 of the next row is started. By sequentially repeating these operations, the signal charges in the pixels 50 of all the rows are read.

When the signal charges of all the rows are read, image data indicating an X-ray image of one screen is recorded in the memory 47. The image data is read from the memory 47 and is output to the console 14 via the communication unit 45. In this way, the X-ray image of a subject M is detected.

The control unit 46 controls the FPD 40 to perform a reset operation and returns an irradiation permission signal to the source controller 11, when receiving an inquiry signal from the control unit 31 of the source controller 11. Then, the operation of the FPD 40 is switched from the reset operation to the accumulating operation at the time of receiving the irradiation start signal.

The FPD 40 includes plural detection pixels 65, which are short-circuited to the signal lines 57 without passing through the TFTs 52, in the same imaging plane 41 in addition to the pixels 50 connected to the signal lines 57 via the TFTs 52 as described above. A detection pixel 65 is a pixel used to detect the dose of X-rays passing through a subject M and incident on the imaging plane 41 and serves as an irradiation start sensor or serves as an irradiation end detection sensor and an AEC sensor. The detection pixels 65 occupy several % of the pixels 50 in the imaging plane 41.

Figure 4:
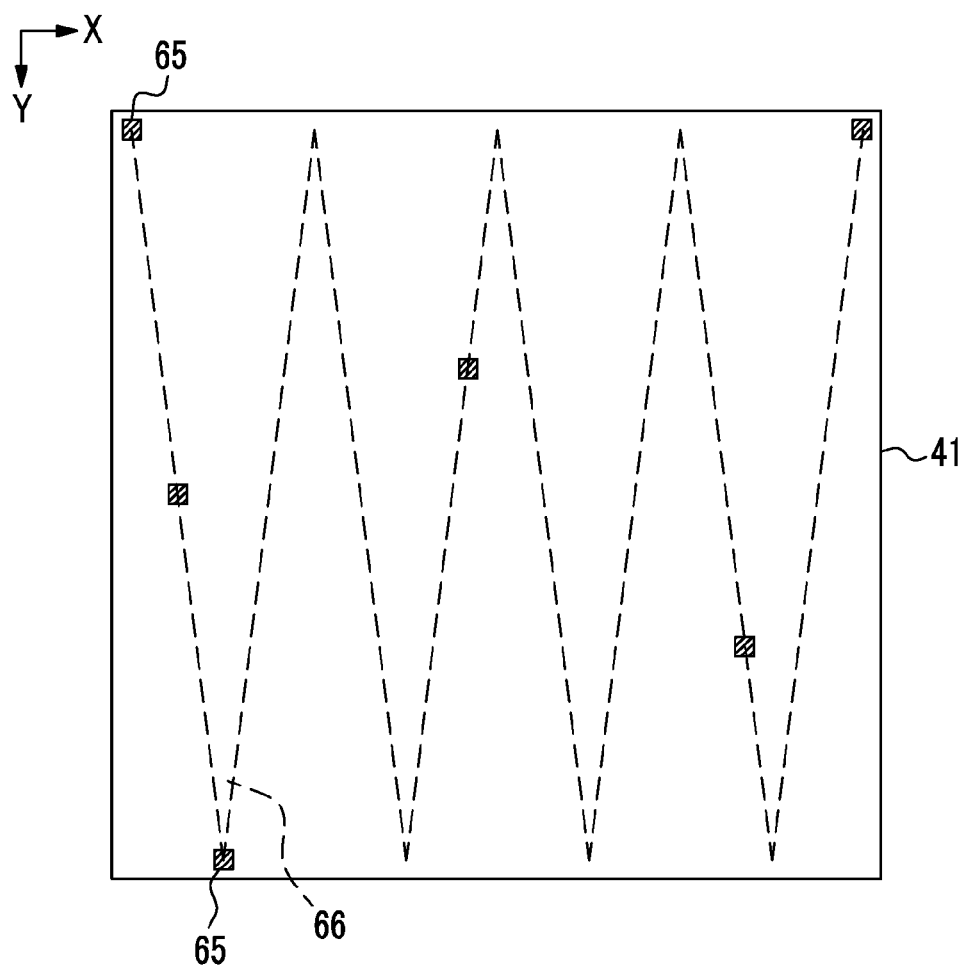
FIG. 4 is a diagram illustrating the arrangement of detection pixels of an FPD of the electronic cassette.

As shown in FIG. 4, the detection pixels 65 are arranged in a waveform locus 66 indicated by a dotted line symmetric about the center of the imaging plane 41 so as to be evenly scattered in the imaging plane 41 without locally deviating in the imaging plane 41. The detection pixel 65 is provided for each column of the pixels 50 connected to the same signal line 57. The columns having the detection pixel 65 are arranged, for example, every two or three columns in which the detection pixel 65 is not disposed. The positions of the detection pixels 65 are known at the time of manufacturing the FPD 40. The FPD 40 stores the positions (coordinates) of all the detection pixels 65 in a nonvolatile memory (not shown). The arrangement of the detection pixels 65 described herein is only an example, and can be appropriately changed.

Since the detection pixel 65 does not include the TFT 52 between the corresponding signal line 57 and the detection pixel and is directly connected to the corresponding signal line 57, the signal charges generated from the detection pixels 65 are read to the signal line 57 immediately. The same is also true when the pixels 50 in the same column are performing the accumulating operation of accumulating by turning off the TFTs 52. Accordingly, the charges generated from the detection pixel 65 always flows in the integration amplifier 60 in the signal line 57 connected to the detection pixel 65. In the accumulating operation, charges from the detection pixels 65 accumulated in the integration amplifier 60 are output as a voltage value to the A/D converter 62 via the MUX 61 at a predetermined sampling cycle.

In FIG. 3, the driving of the AEC unit 67 is controlled by the control unit 46. The AEC unit 67 acquires a voltage value (referred to as a dose detection signal) from the signal line 57 connected to the detection pixel 65 via the A/D converter 62. The density adjusting unit constitutes a part of the AEC unit 67.

Figure 5:
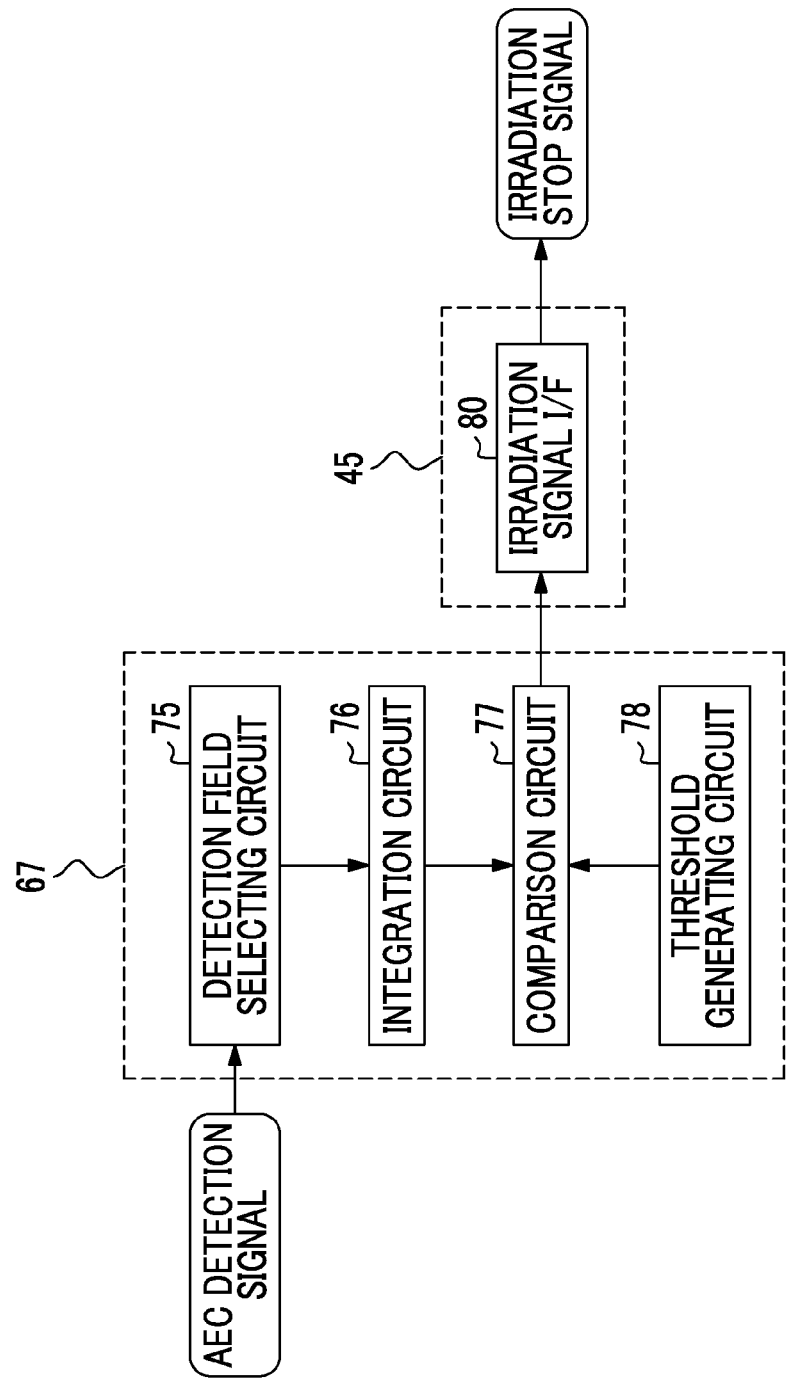
FIG. 5 is a block diagram illustrating the internal constitutions of an AEC unit and a communication unit of the electronic cassette.

In FIG. 5, the AEC unit 67 includes a detection field selecting circuit 75, an integration circuit 76, a comparison circuit 77, and a threshold generating circuit 78. The detection field selecting circuit 75 selects the dose detection signals of what detection pixels 65 should be used for the AEC out of plural detection pixels 65 distributed in the imaging plane 41 on the basis of the information of the detection field from the console 14. The integration circuit 76 integrates the dose detection signals from the detection pixels 65 selected by the detection field selecting circuit 75. The comparison circuit 77 starts monitoring the integrated value of the dose detection signal from the integration circuit 76 when the irradiation start with X-rays is detected. The integrated value is compared with the irradiation stop threshold given from the threshold generating circuit 78 at an appropriate time. When the integrated value reaches the threshold, the comparison circuit 77 outputs the irradiation stop signal.

The communication unit 45 includes an irradiation signal I/F 80 in addition to the antenna 42 and the socket 44. The irradiation signal I/F 35 of the source controller 11 is connected to the irradiation signal I/F 80. The irradiation signal I/F 80 receives an inquiry signal, transmits the irradiation permission signal in response to the inquiry signal, and transmits the output of the comparison circuit 77, that is, the irradiation stop signal.

The console 14 is connected to the electronic cassette 13 so as to communicate in a wired manner or a wireless manner and controls the operation of the electronic cassette 13. Specifically, the console 14 transmits the radiographing conditions to the electronic cassette 13 to set the conditions (such as the gain of the amplifier amplifying the voltage corresponding to the accumulated signal charges) of the signal process of the FPD 40 and to control the turning-on or turning-off of the power source of the electronic cassette 13, the mode switching to a power saving mode or a radiography standby state, and the like.

The console 14 performs various image processes such as offset correction, gain correction, and defect correction on the X-ray image data transmitted from the electronic cassette 13. In the defect correction, the pixel values of the column having the detection pixel 65 are interpolated with the pixel values of the neighboring columns not having the detection pixel 65. The console 14 reconstructs a series of X-ray images detected by the electronic cassette 13 and generates a tomographic image representing a desired cross-section of the subject M. The tomographic image is displayed on a display 89 (see FIG. 7) of the console 14. The data thereof is stored in a storage device 87 or a memory 86 (see FIG. 7 for both) in the console 14 or a data storage such as an image storage server connected to the console 14 via a network.

The console 14 receives the input of an examination order including information such as gender of a patient, age of a patient, a radiography site, and a radiographing method and displays the examination order on the display 89. The examination order is input from an external system that manages patient information or examination information relevant to radiographic examinations, such as an HIS (Hospital Information System) or an RIS (Radiographic Information System), or is manually input by an operator. The examination order includes radiography sites such as head, chest, and abdomen and radiographing directions such as front, side, oblique, PA (radiation of X-rays from the back of a subject), and AP (radiation of X-rays from the front of a subject). The operator confirms the details of the examination order through the use of the display 89 and inputs the radiographing conditions corresponding to the details through the use of the operation screen of the display 89.

As shown in FIG. 6, in the console 14, radiographing conditions can be set for each radiography site. The radiographing conditions include, for example, a tube voltage and an irradiation stop threshold used to determine the irradiation stop of X-rays through comparison with the integrated value of the dose detection signals of the detection pixels 65. The information of the radiographing conditions is stored in the storage device 87.

Figure 7:
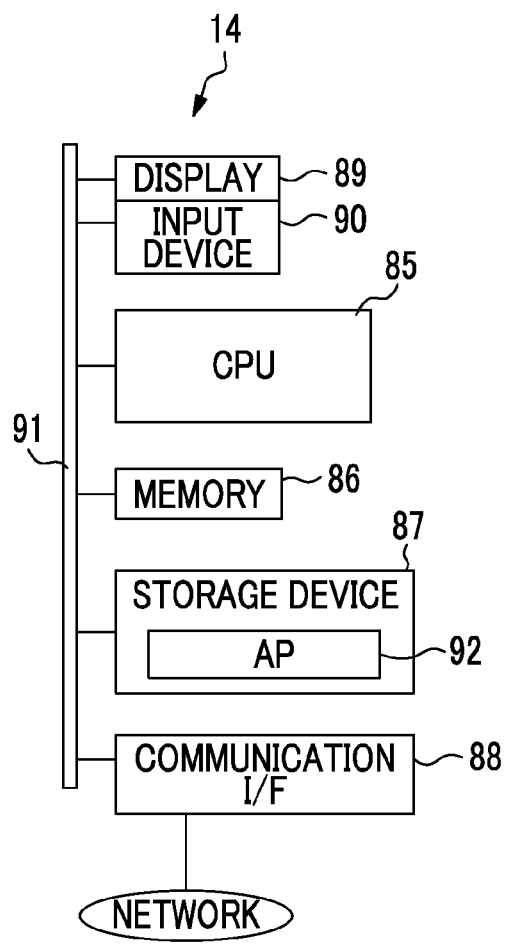
FIG. 7 is a block diagram illustrating the internal constitution of the console.

In FIG. 7, a computer constituting the console 14 includes a CPU 85, a memory 86, a storage device 87, a communication I/F 88, a display 89, and an input device 90. These are connected to each other via a data bus 91. The region of interest setting unit constitutes a part of the console 14.

The storage device 87 is, for example, an HDD (Hard Disk Drive). The storage device 87 stores control programs or application programs (hereinafter, referred to as AP) 92. The AP 92 is a program causing the console 14 to perform various functions relevant to the radiography such as the examination order, the display process of an X-ray image, the image process on the X-ray image, and the setting of the radiographing conditions.

The memory 86 is a work memory in which the CPU 85 performs processes. The CPU 85 loads the control program stored in the storage device 87 into the memory 86 and performs the processes based on the program, thereby generally controlling the units of the computer. The communication I/F 88 is a network interface controlling the wired or wireless transmission to the external apparatuses such as the RIS, the HIS, the image storage server, and the electronic cassette 13.

The input device 90 includes a keyboard, a mouse, or a touch panel coupled to the display 89. Through the use of the input device 90, the radiographing conditions, the distance (SID: Source Image Distance, see FIG. 1) from the position Z0 on the imaging plane 41 in the direction perpendicular to the imaging plane 41 of the FPD 40 to the position Z1 of the focal point of the X-ray tube 17, ROI information, and the like are input. The ROI information is information such as the position, the size, and the height form the radiography platform 15 of a region of interest (ROI) of a subject M to be subjected to the tomosynthesis imaging. The position and the size of the ROI are input, for example, as XY coordinates based on the central position of the imaging plane of the electronic cassette 13. The height from the radiography platform 15 may be a specific numerical value when the numerical value is known, or may be selected from predetermined several steps of range set values.

Figure 8:
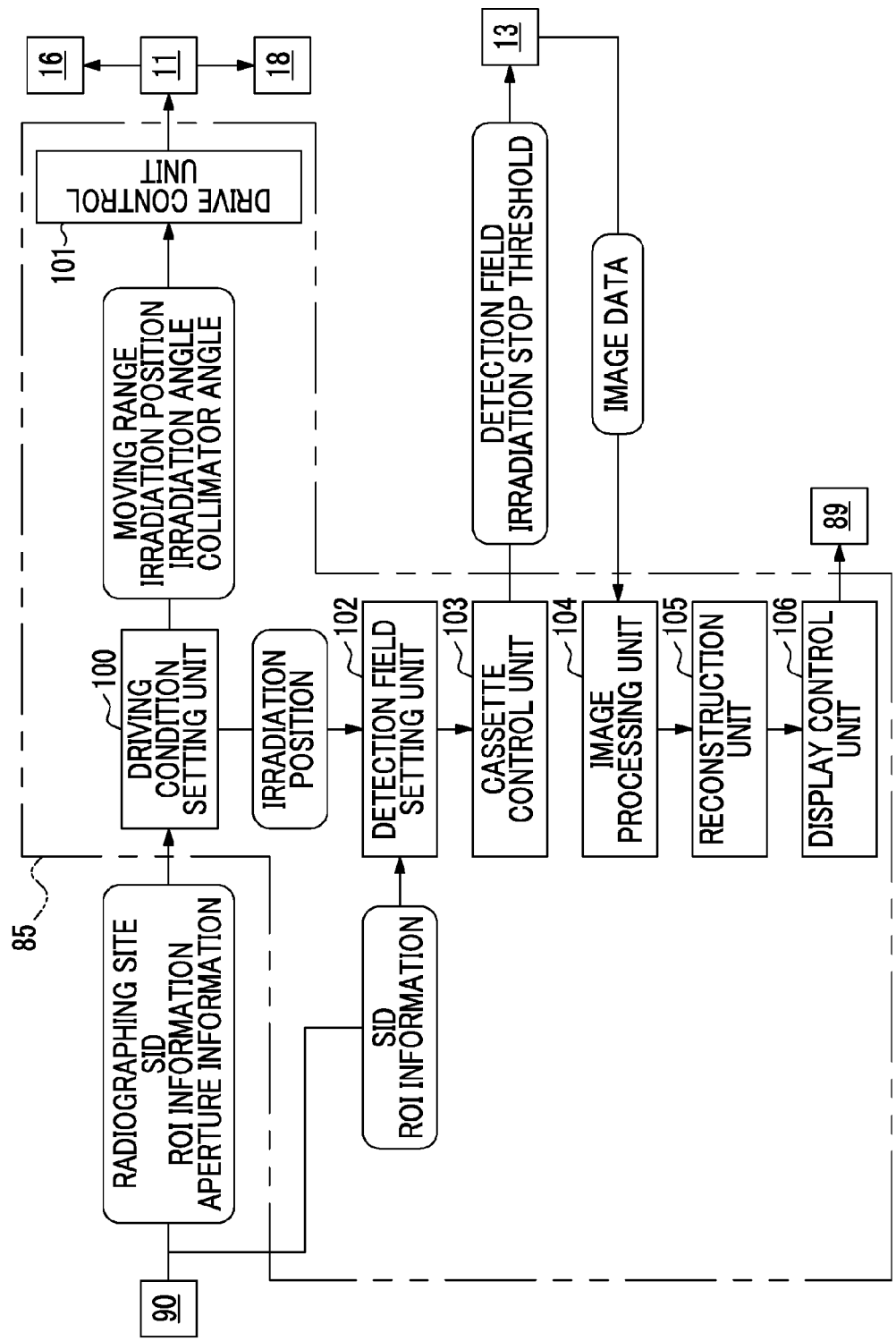
FIG. 8 is a block diagram illustrating the functions of the console and the flow of information.

In FIG. 8, the CPU 85 of the console 14 serves as a driving condition setting unit 100, a drive controller 101, a detection field setting unit 102, a cassette controller 103, an image processing unit 104, a reconstruction unit 105, and a display controller 106, when the AP 92 is started up to select the tomosynthesis imaging.

The driving condition setting unit 100 sets the movement range of the X-ray source 10 during the tomosynthesis imaging, the irradiation positions and irradiation angles in the movement range, and the collimator angle which is an opening angle of the irradiation field limiter 18 on the basis of the radiographing site and the ROI information. The driving condition setting unit 100 sets the movement range of the X-ray source 10 depending on the size of the ROI. For example, the movement range of the X-ray source 10 is set to be large when the size of the ROI is large, and the movement range of the X-ray source 10 is set to be small when the size of the ROI is small. The driving condition setting unit 100 sets the number of radiographing operations necessary for acquiring a tomographic image depending on the radiographing site, and sets the irradiation positions and the irradiation angles of the X-ray source 10 on the basis of the set number of radiographing operations. For example, the number of radiographing operations is set to be large for the radiographing site requiring a fine tomographic image, and the number of radiographing operations is set to be small for the radiographing site not requiring a fine tomographic image.

Figure 9:
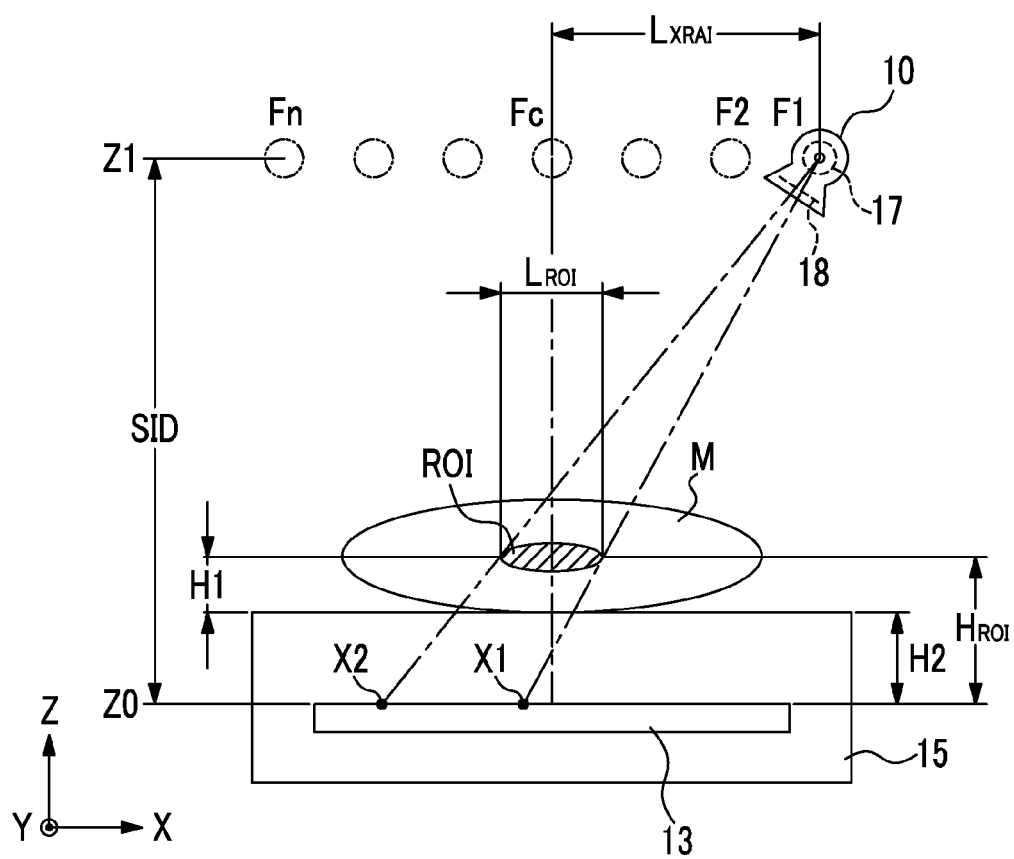
FIG. 9 is a diagram illustrating a detection field acquired from an irradiation position of an X-ray source and ROI information.

As shown in FIG. 9, the movement range and the irradiation position of the X-ray source 10 are set as XY coordinates based on a reference position Fc of the X-ray source 10 opposing the center of the imaging plane of the electronic caste 13. The irradiation angle of the X-ray source 10 is set to an angle defined by a reference line extending in the Z direction from the irradiation position of the X-ray source 10 and an irradiation line extending from the irradiation position to the center of the ROI. The drive controller 101 drives the source moving mechanism 16 and the irradiation field limiter 18 through the use of the source controller 11 on the basis of various driving conditions set by the driving condition setting unit 100.

The detection field setting unit 102 sets the detection field at the respective irradiation positions on the basis of the SID and the ROI information input from the input device 90 and the irradiation positions of the X-ray source 10 set by the driving condition setting unit 100. For example, when the detection field at the irradiation position F1 shown in FIG. 9 is set, the detection field setting unit 102 calculates distances X1 and X2 to both edges in the X direction of the detection field using "SID", "$H_{ROI}$", "$L_{ROI}$", "$L_{XRAI}$", and Expressions 1 and 2. The distances X1 and X2 are distances from the X-ray source 10 in the direction in which the X-ray source 10 oscillates, where the position of the X-ray source 10 for each radiographing operation is set as an origin. The distance X1 is a distance from the X-ray source 10 to an edge of the detection field close to the X-ray source 10 and the distance X2 is a distance from the X-ray source 10 to an edge of the detection field distant from the X-ray source 10. The position of the detection field on the imaging plane 41 of the FPD 40 is specified from the distances X1 and X2 and the relative position information between the X-ray source 10 and the electronic cassette 13.

"$H_{ROI}$" represents the height from the imaging plane 41 of the FPD 40 to the ROI and is a value obtained by adding the height H2, which is stored in advance in the detection field setting unit 102, from the imaging plane 41 to the top surface of the radiography platform 15 to the height H1, which is input as the ROI information from the top surface of the radiography platform 15 to the ROI. "$L_{ROI}$" represents the size of the ROI in the X direction which is the moving direction of the X-ray source 10 and a value input as the ROI information is used. "$L_{XRAI}$" represents position information in the moving direction of the X-ray source 10 relative to the central axis of the ROI in the direction perpendicular to the imaging plane 41 of the FPD 40 and is calculated on the basis of the position in the X direction of the X-ray source 10 set by the driving condition setting unit 100, the position of the ROI input as the ROI information, and the above-mentioned "$L_{ROI}$". The detection field setting unit 102 sets the detection field at the overall irradiation positions of the X-ray source 10 similarly. As the coordinate in the Y direction of the detection field, the position and the size in the Y direction of the ROI input as the ROI information are used without any change.

$$X1 = SID/(SID-H_{ROI}) \times (L_{XRAI} - L_{ROI}/2) \quad (1)$$

$$X2 = SID/(SID-H_{ROI}) \times (L_{XRAI} + L_{ROI}/2) \quad (2)$$

The cassette controller 103 supplies the detection field set by the detection field setting unit 102 and the information of the irradiation stop threshold to the electronic cassette 13. The detection field selecting circuit 75 selects a detection field of each radiographing operation of the tomosynthesis imaging on the basis of the information of the detection field supplied from the cassette controller 103. The threshold generating circuit 78 generates the irradiation stop threshold for each radiographing operation of the tomosynthesis imaging on the basis of the information of the irradiation stop threshold supplied from the cassette controller 103.

The image processing unit 104 performs various image processes such as the offset correction, the gain correction, and the defect correction on a series of X-ray images input from the electronic cassette 13. The reconstruction unit 105 adds the series of X-ray images to generate a tomographic image of the ROI of the subject M. The display controller 106 controls the display 89 to display the tomographic image or operation menus necessary for the radiographing.

Figure 11:
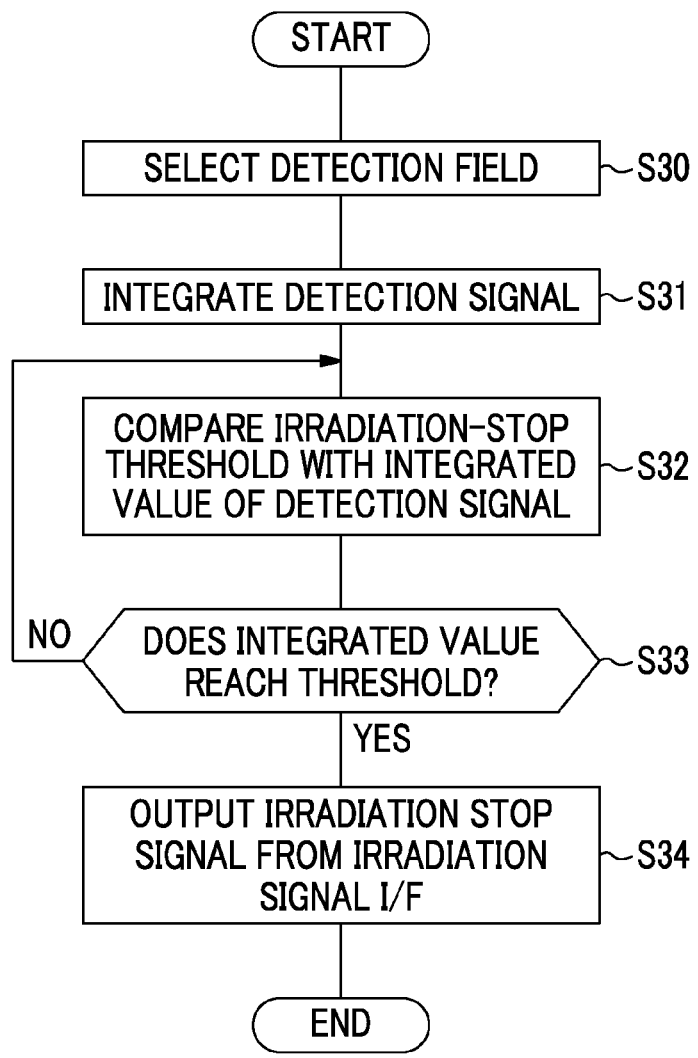
FIG. 11 is a flowchart illustrating the flow of processes of an AEC.

The flow of processes of performing a tomosynthesis imaging in the radiographic system 2 will be described below with reference to the flowchart shown in FIGS. 10 and 11.

First, the X-ray source 10 and the radiography platform 15 are located at appropriate positions for the radiographing, the SID is measured as indicated by step 10 (S10) of FIG. 10, and the measured value is input to the console 14 through the use of the input device 90. Subsequently, a subject M is placed on the radiography platform 15, and the input device 90 is operated to input the ROI information including the position, the size, and the height of the ROI of the subject M to the console 14 (S11).

When the SID is input as being invariable, or when a position sensor including a potentiometer detecting the height positions of the X-ray source 10 and the radiography platform 15 is provided and the SID can be automatically calculated on the basis of the output of the position sensor, the process of step S10 may be omitted.

The radiographing site, the measured value of the SID, and the ROI information are input to the driving condition setting unit 100. In the driving condition setting unit 100, the movement range, the irradiation position, the irradiation angle, and the collimator angle of the X-ray source 10 are set on the basis of various input parameters (S12). This information is output to the drive controller 101 or the like.

The measured value of the SID, the ROT information, and the irradiation position are input to the detection field setting unit 102. In the detection field setting unit 102, the detection fields at the overall irradiation positions are set on the basis of various input parameters (S13). The detection field is transmitted to the electronic cassette 13 along with the irradiation stop threshold by the cassette controller 103.

Subsequently, under the control of the drive controller 101, the source moving mechanism 16 is driven and the X-ray source 10 moves to the first irradiation position F1. The irradiation field limiter 18 is driven by the source controller 11 and the irradiation field is adjusted so as to satisfy the collimator angle set by the driving condition setting unit 100 (S14).

Thereafter, the radiographic system 2 waits for an irradiation start instruction (S15). When the irradiation switch 12 is operated by an operator to give the irradiation start instruction (YES in S15), the irradiation with X-rays from the X-ray source 10 is started and thus the FPD 40 starts the charge accumulating operation to perform the first radiographing operation (S16).

In the electronic cassette 13, the AEC unit 67 performs an AEC based on the output of the detection pixels 65 at the same time as performing the accumulating operation of the FPD 40. As shown in FIG. 11, the detection field selecting circuit 75 selects the dose detection signals from the detection pixels 65 existing in the detection field out of the dose detection signals of plural detection pixels 65 input from the A/D converter 62 on the basis of the information of the detection field at the first irradiation position F 1 given from the cassette controller 103 of the console 14, and outputs the selected dose detection signal to the integration circuit 76 (S30). The integration circuit 76 integrates the detection signals (S31).

The threshold generating circuit 78 generates the irradiation stop threshold supplied from the cassette controller 103 and outputs the generated irradiation stop threshold to the comparison circuit 77. The comparison circuit 77 compares the irradiation-stop threshold value from the threshold generating circuit 78 with the integrated value of the detection signal from the integration circuit 76 (S32), and outputs the irradiation stop signal when the integrated value reaches the threshold value (YES in S33). The irradiation stop signal output from the comparison circuit 77 is transmitted to the irradiation signal I/F 35 of the source controller 11 via the irradiation signal I/F 80 (S34).

When receiving the irradiation stop signal through the irradiation signal I/F 35, the control unit 31 of the source controller 11 stops the supply of power from the high voltage generator 30 to the X-ray source 10 and thus stops the irradiation with X-rays. In the electronic cassette 13, the operation of the FPD 40 is changed from the accumulating operation to the reading operation and image data is output through the reading operation.

The image data output from the FPD 40 is transmitted to the console 14 through the communication unit 45 in a wired or wireless manner, and various image processes are performed by the image processing unit 104. In the first radiographing operation, image data I1 is acquired (S17 in FIG. 10).

After the first radiographing operation, the X-ray source 10 moves to the second irradiation position F2 (S18) and the second radiographing operation is performed at the irradiation position F2 (S19). At this time, the AEC unit 67 selects the dose detection signals from the detection pixels 65 existing in the detection field out of the dose detection signals of plural detection pixels 65 input from the A/D converter 62 on the basis of the information of the detection field at the second irradiation position F2 supplied from the cassette controller 103, and performs the processes of S30 to S34 in FIG. 11 thereon, similarly to the first radiographing operation, whereby image data I2 is acquired (S20 in FIG. 10). Similarly, at the third to n-th irradiation positions F3 to Fn, the radiographing operations using the detection fields set depending on the irradiation positions are performed, whereby image data In are acquired (S21).

After the n-th radiographing operation is ended, the image data I1, I2, ..., In acquired at the irradiation positions F1 and F2 to Fn are added by the reconstruction unit 105 to generate a tomographic image of the ROI of the subject M (S22). The data of the generated tomographic image is displayed on the display 89 by the display controller 106.

As described above, according to this embodiment, since the AEC is performed in the respective radiographing operations of the tomosynthesis imaging, it is possible to make the densities of the detection fields of a series of X-ray images acquired through the radiographing operations constant and thus to acquire a tomographic image with high image quality. Since the AEC of each radiographing operation uses a detection field set depending on the irradiation position of the X-ray source 10, it is possible to radiograph the ROI of a subject M with an appropriate density. Since the detection field is automatically set on the basis of the irradiation position of the X-ray source 10 and the ROI information, it is possible to simply and rapidly set the detection field.

The present invention is not limited to the above-mentioned embodiment, but can employ various constitutions without departing from the concept of the present invention.

Figure 12:
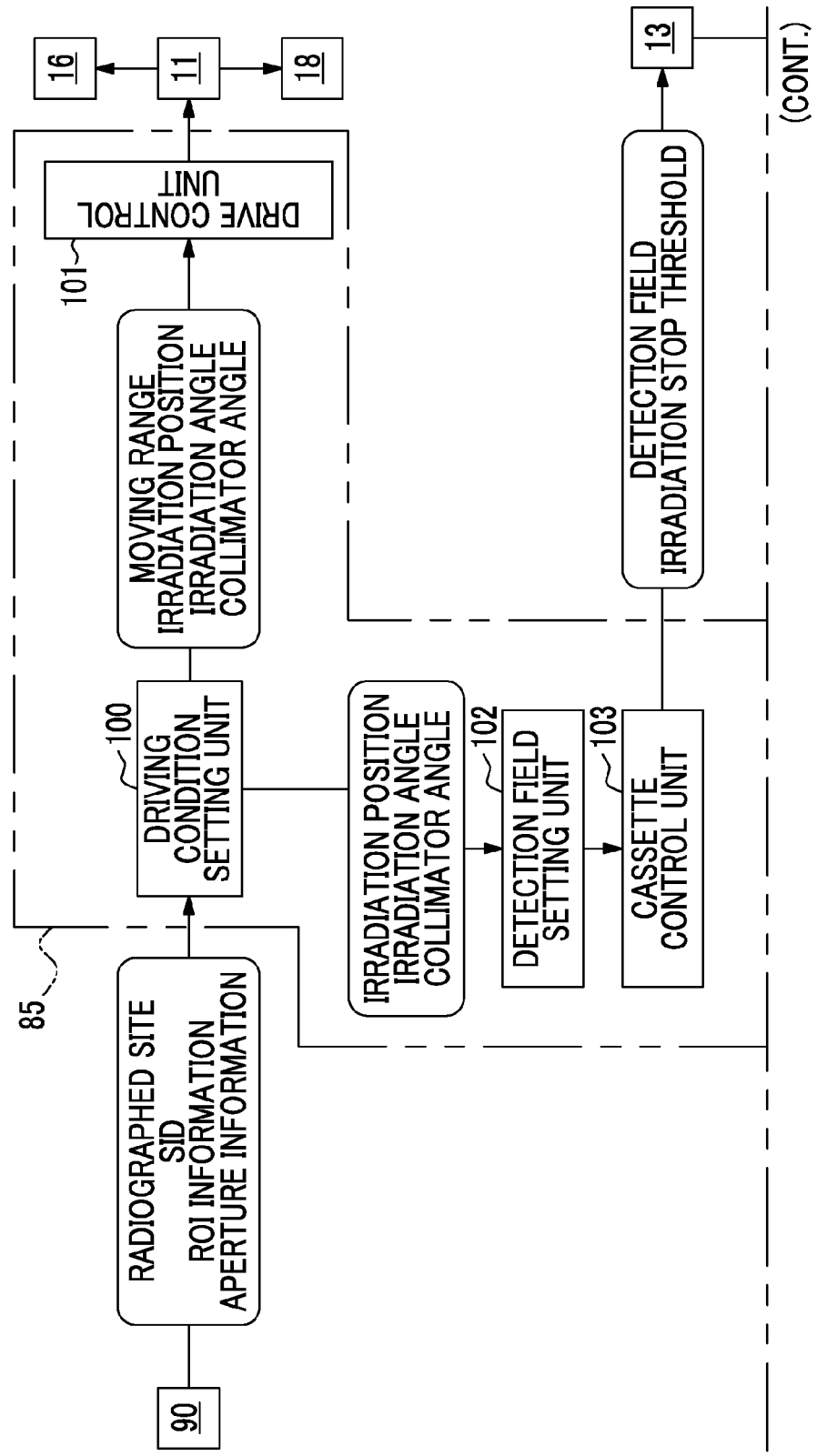
FIG. 12 is a block diagram illustrating the functions of the console and the flow of information for setting a detection field from an irradiation field.

In the above-mentioned embodiment, it is stated that the detection field at each irradiation position is set on the basis of the ROI information including the position, the size, and the height of the ROI, but the detection field at each irradiation position may be set on the basis of the irradiation field of X-rays defined by the irradiation field limiter 18. For example, as shown in FIG. 12, in the tomosynthesis imaging according to this embodiment, the irradiation positions, the irradiation angles, and the collimator angles of the X-ray source 10 set by the driving condition setting unit 100 are input to the detection field setting unit 102.

Figure 13:
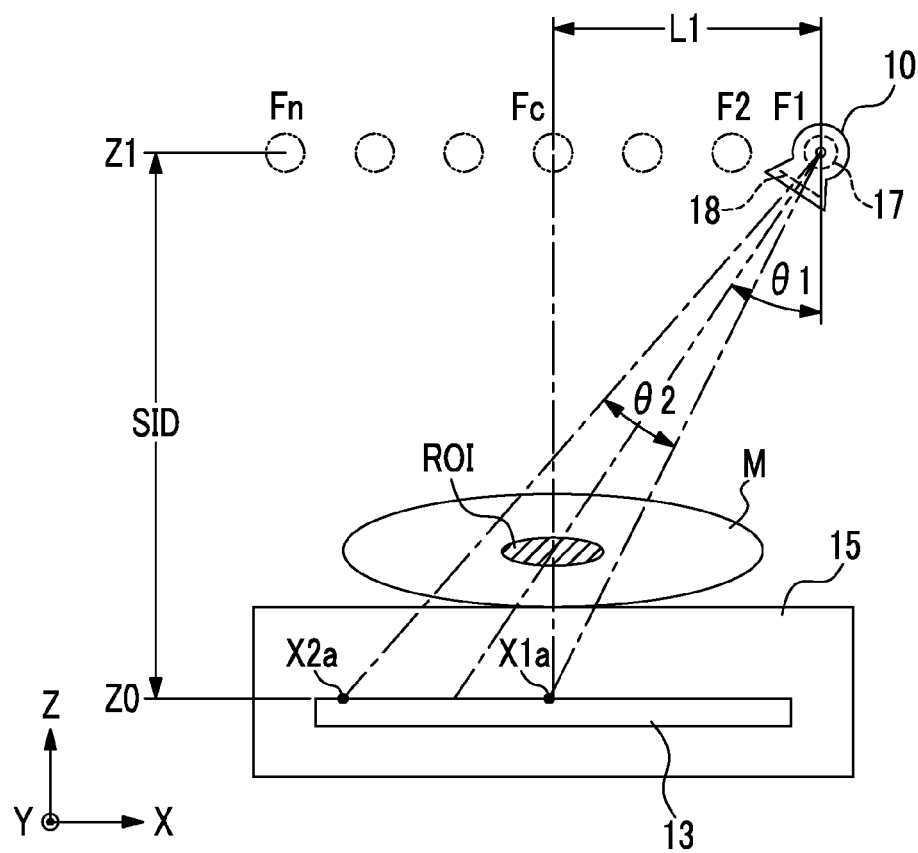
FIG. 13 is a diagram illustrating a detection field acquired from an irradiation position of an X-ray source and an irradiation field.

When the detection field at the irradiation position F1 shown in FIG. 13 is set, the detection field setting unit 102 calculates the distances X1a and X2a to both edges in the X direction of the detection field using "SID", "L1", "θ1", "θ2", and Expressions 3 and 4. The distances X1a and X2a are distances from the X-ray source 10 in the direction in which the X-ray source 10 oscillates, where the position of the X-ray source 10 for each radiographing operation is set as an origin. The distance X1a is a distance from the X-ray source 10 to an edge of the detection field close to the X-ray source 10 and the distance X2a is a distance from the X-ray source 10 to an edge of the detection field distant from the X-ray source 10. The position of the detection field on the imaging plane 41 of the electronic cassette 13 is specified from the distances X1a and X2a and the relative position information between the X-ray source 10 and the electronic cassette 13.

"L1" represents position information in the X direction with respect to the central position of the imaging plane 41 of the FPD 40. "θ1" represents an oscillation angle relative to the state where the X-ray source 10 is vertically suspended. "θ2" represents a collimator angle of the irradiation field limiter 18. "L1", "θ1", and "θ" uses the values set by the driving condition setting unit 100. The detection field setting unit 102 similarly sets the detection fields at the overall irradiation positions of the X-ray source 10. The coordinate in the Y direction of the detection field can be calculated from the SID and the collimator angle θ2.

$$X1a = SID \cdot \tan(\theta1 - \theta2/2) \quad (3)$$

$$X2a = SID \cdot \tan(\theta1 + \theta2/2) \quad (4)$$

According to this embodiment, since the AEC is performed using the detection pixels 65 in the irradiation field of X-rays, it is possible to make the densities of the detection fields of a series of X-ray images acquired through the radiographing operations constant and thus to acquire a tomographic image with high image quality. Since the detection field is automatically set on the basis of the irradiation position and the collimator angle of the X-ray source 10, it is possible to simply and rapidly set the detection field.

Figure 14:
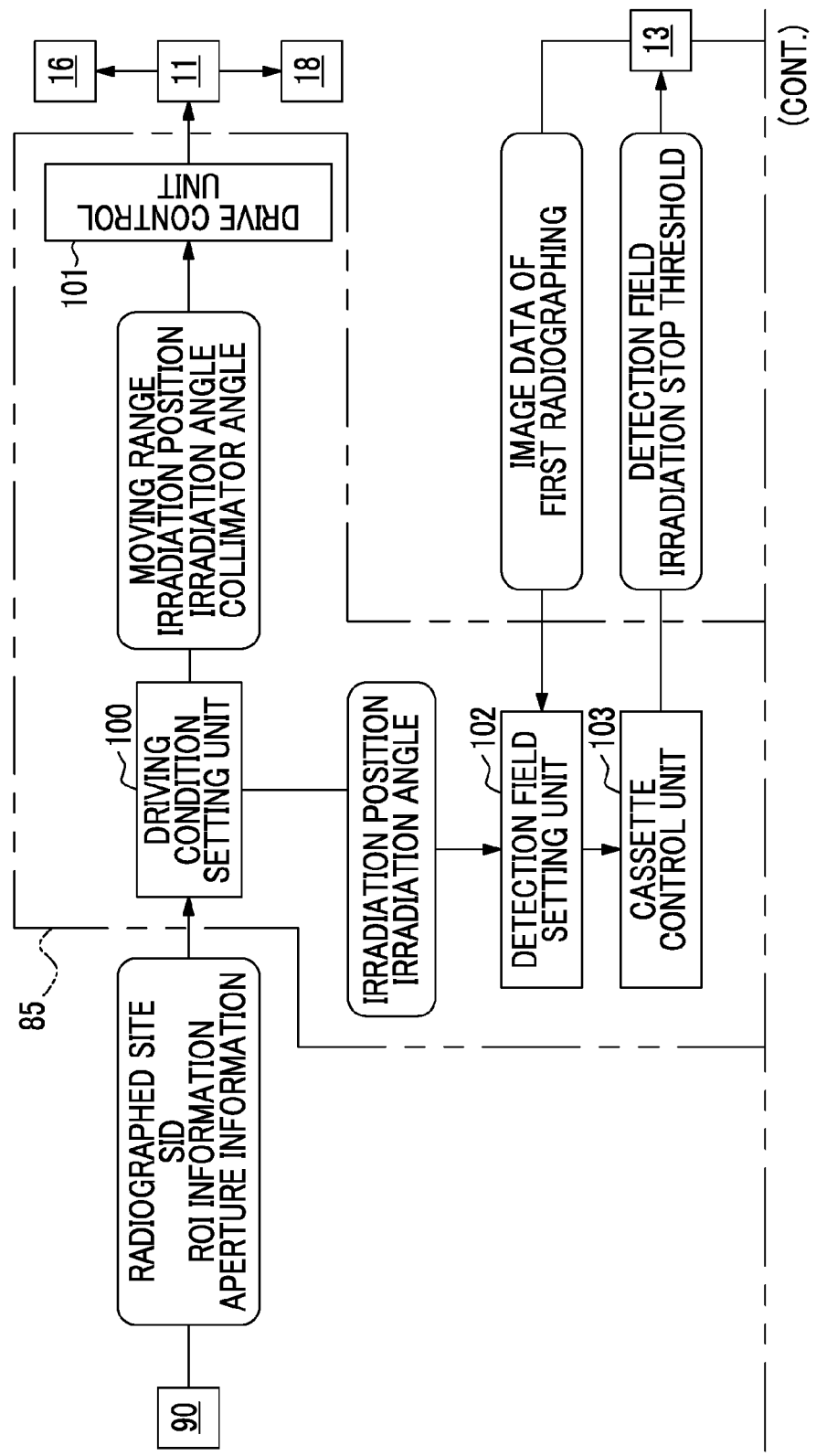
FIG. 14 is a block diagram illustrating the functions of the console and the flow of information for setting a detection field for second or subsequent radiographing from an X-ray image acquired through first radiographing.
Figure 15:
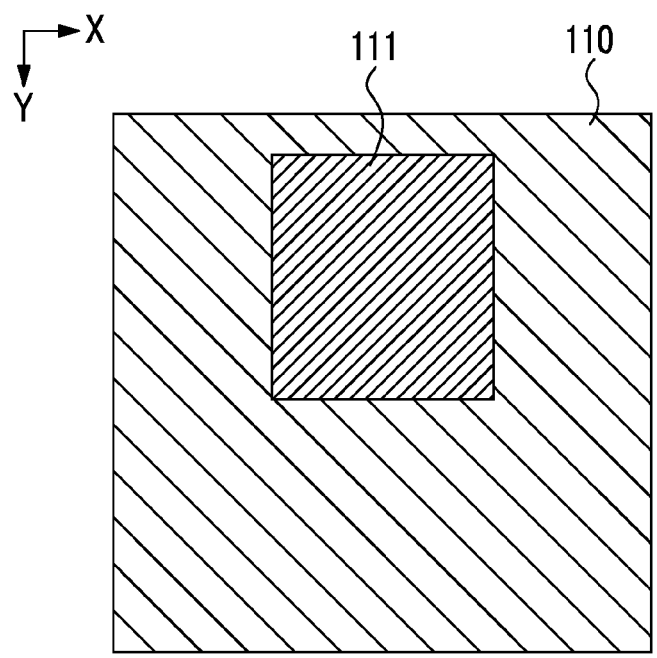
FIG. 15 is a diagram illustrating a state where an irradiation field is specified from the X-ray image acquired through first radiographing.

In the above-mentioned embodiments, the detection field is calculated and set for each irradiation position of the X-ray source 10, but the detection field to be used for the second or subsequent radiographing operation may be set by analyzing the X-ray image acquired through the first radiographing operation. For example, as shown in FIG. 14, when the tomosynthesis imaging is performed, the image data of the first radiographing operation is input from the electronic cassette 13 to the detection field setting unit 102. As shown in FIG. 15, the detection field setting unit 102 analyzes the input image data 110 and specifies the irradiation field 111 of X-rays from the pixels values of the pixels. The detection field setting unit 102 geometrically calculates and sets the detection field to be used for the second or subsequent radiographing operation using "SID", "$H_{ROI}$", "$L_{ROI}$", and "$L_{ROI}$" on the basis of the specified irradiation field 111 and the irradiation position and the irradiation angle input from the driving condition setting unit 100, similarly to the above-mentioned embodiments.

According to this embodiment, since the AEC of the second or subsequent radiographing operation is performed using the detection field set from the analysis result of the X-ray image acquired through the first radiographing operation, it is possible to make the densities of the detection fields of a series of X-ray images acquired through the radiographing operations constant and thus to acquire a tomographic image with high image quality. Since the detection field to be used for the second or subsequent radiographing operation can be set by calculation, it is possible to more simply and rapidly set the detection field, compared with a case where the X-ray images of all the radiographing operations are analyzed to extract the detection field and the radiographing operations are performed. This is because the calculation of a case where the position of the detection field is geometrically calculated using the position of the source and the ROI i In addition to the example where the X-ray source 10 is made to move along a straight trajectory in the X direction parallel to the detection plane of the electronic cassette 13 by the source moving mechanism 16, even when the X-ray source 10 and the electronic cassette 13 are made to synchronously move in the opposite directions with a subject M interposed therebetween, the detection field of the respective radiographing operations can be similarly calculated using the position of the X-ray source, the ROI information, and the electronic cassette 13. In this case, since the electronic cassette 13 moves, the central position of the detection field does not vary in the radiographing operations, but the size of the detection field varies in the radiographing operations. That is, for example, compared with the position Fc shown in FIG. 1, in case of the position F1 at which an angle is applied to the X-ray source 10, the central position of the detection field on the electronic cassette 13 does not vary but the size of the detection field in the X-direction increases.

In this embodiment, the AEC is used to make the densities of the detection fields of a series of X-ray images acquired through the tomosynthesis imaging constant, but the densities of the detection fields of the series of X-ray images may be adjusted by change of a gain of the integration amplifier during the reading operation. In this case, as shown in FIG. 16, a gain-variable integration amplifier 150 is used instead of the integration amplifier 60.

Figure 16:
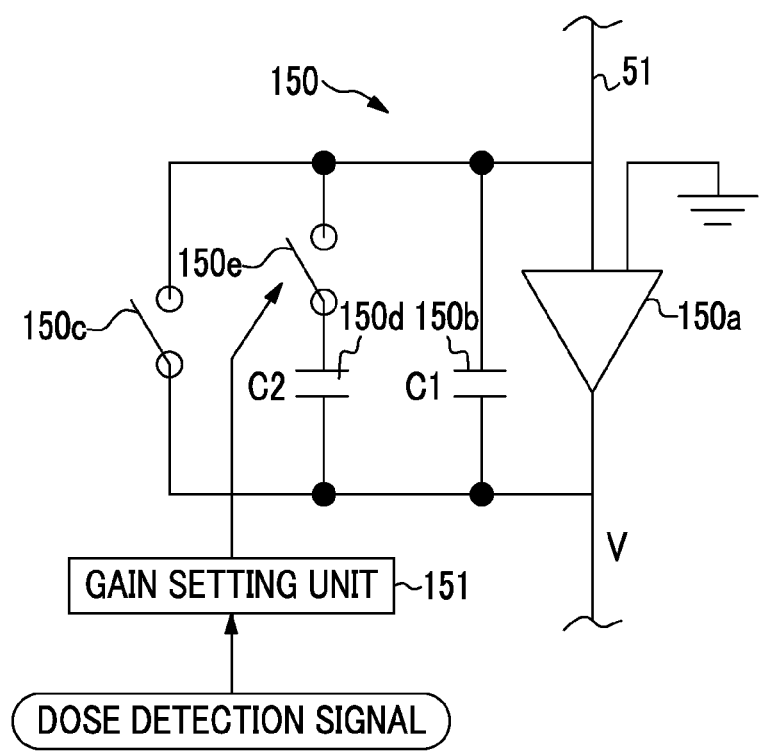
FIG. 16 is a diagram illustrating the constitution for setting a gain of an integration amplifier during a reading operation.

In FIG. 16, the integration amplifier 150 includes an operational amplifier 150a and a reset switch 150c, similarly to the integration amplifier 60. Two capacitors 150b and 150d are connected between the input and output terminals of the operational amplifier 150a, and a gain change switch 150e is connected to the capacitor 150d. An output voltage signal V from the integration amplifier is $V = q/(C1+C2)$ when the gain change switch 150e is turned on and is $V = q/C1$ when the gain change switch 150e is turned off. Here, q represents the accumulated charges, and C1 and C2 represent the capacitance values of the capacitors 150b and 150d, respectively. By switching the ON/OFF of the gain change switch 150e in this way, it is possible to change the gain of the integration amplifier 150. Here, an example where two capacitors are connected and the gain is changed in two steps is described, but it is preferable that the gain can be changed in two or more steps by connecting two or more capacitors or by using a capacitance-variable capacitor as the capacitor.

The gain setting unit 151 is disposed in the FPD instead of the AEC unit 67. The gain setting unit 151 operates to control the operation of the gain change switch 150e during the reading operation when the FPD starts the accumulating operation. The dose detection signal is periodically input to the gain setting unit 151 from the signal processing circuit 59. The gain setting unit 151 sets the gain of the integration amplifier 150 to the minimum value when outputting the dose detection signal so as not to saturate the dose detection signal. In this example, the gain change switch 150e is turned on.

Similarly to the AEC unit 67, the gain setting unit 151 integrates the total value, the average value, the maximum value or the largest frequency of the dose detection signal from the detection pixels 65 existing in the detection field set by the detection field setting unit 102 by a predetermined number of times, and compares the integrated value with a predetermined threshold. When the integrated value is larger than the threshold, the gain setting unit 151 turns on the gain change switch 150e during the reading operation. On the other hand, when the cumulative dose reaching a portion in the detection field in the imaging plane 41 is low and the integrated value is smaller than or equal to the threshold, the gain change switch 150e is turned off during the reading operation to raise the gain of the integration amplifier 150. More specifically, the gain of the integration amplifier 150 is set so that the maximum value and the minimum value of the output voltage signal V of the detection field are matched with the maximum value and the minimum value of the range for the A/D conversion.

Since the gain setting unit 151 maintains the density balance of the detection field of a series of X-ray images acquired through the tomosynthesis imaging and suppress an artifact such as a virtual outline during reconstruction, it is preferable that a series of X-ray images be multiplied by the reciprocal of the gain for normalization.

In the radiographing operation in which the cumulative dose of X-rays is set to be low, the width of the maximum value and the minimum value of the voltage signal V is smaller than the range for A/D conversion, and the acquired X-ray image is an indistinct image with conspicuous noise. However, by raising the gain of the integration amplifier when the cumulative dose reaching the portion in the detection field is low, it is possible to obtain an X-ray image with high image quality and with inconspicuous noise. Accordingly, it is possible to suppress the irradiation dose set in the X-ray source and thus to achieve a special effect of reducing the exposure of a patient. The irradiation stop threshold of the AEC may be set to be low to rapidly stop the irradiation with X-rays and the insufficient dose may be replenished by raising the gain of the integration amplifier. In this case, it is also possible to reduce the exposure of a patient.

In the above-mentioned embodiment, since the pixels 50 for image detection and the detection pixels 65 serving as an AEC sensor independently exist, it is necessary to perform a defect correction of interpolating the pixel value of a column in which the detection pixel 65 is located with the pixel value of a neighboring column in which the detection pixel 65 is not located. Accordingly, the degradation in image quality of an X-ray image may be caused. Therefore, the defect correction is made to be unnecessary by constructing the FPD with the constitution of the FPD 160 shown in FIG. 17.

Figure 17:
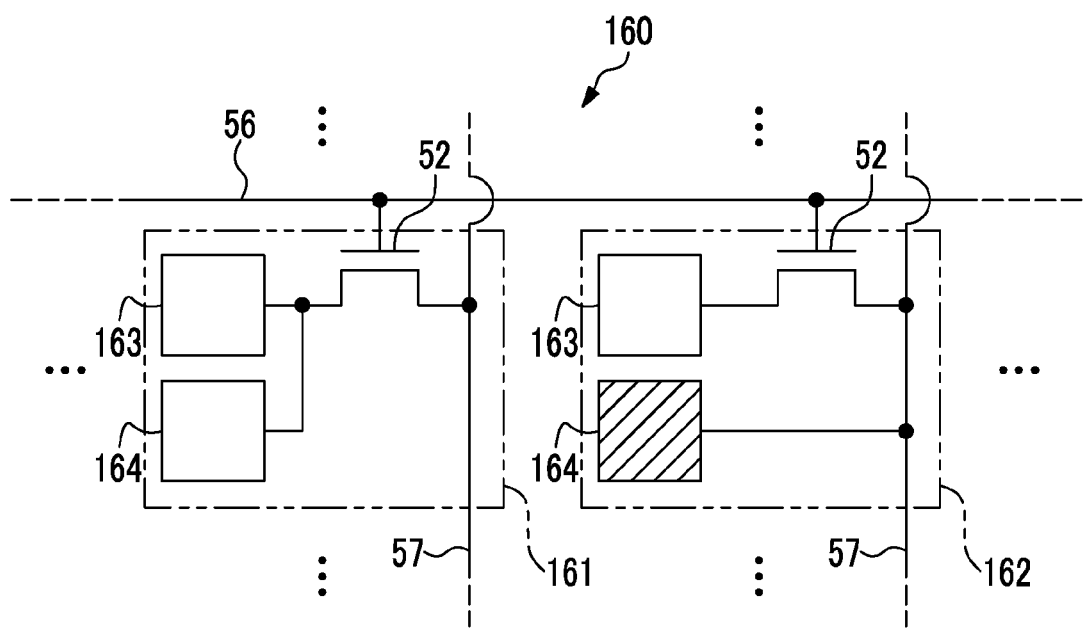
FIG. 17 is a diagram illustrating another example of an FPD.

In FIG. 17, the FPD 160 includes first pixels 161 for image detection and second pixels 162 for image detection and AEC. The first and second pixels 161 and 162 are arranged in a matrix shape at an appropriate ratio, similarly to the pixels 50 and the detection pixels 65 of the above-mentioned embodiment. Each of the first and second pixels 161 and 162 includes two photodiodes 163 and 164. The photodiode 163 and 164 of the first pixel 161 are connected in parallel, and one end is connected to the signal line 57 via the TFT 52. On the other hand, one end of the photodiode 163 of the second pixel 162 is connected to the signal line 57 via the TFT 52, similarly to the first pixel 161, but the photodiode 164 is directly connected to the signal line 57 without passing through the TFT 52. That is, the photodiode 164 of the second pixel 162 has the same constitution as the detection pixel 65 in the above-mentioned embodiment.

Charges accumulated in two photodiodes 163 and 164 are read from the first pixel 161. On the other hand, only charges accumulated in the photodiode 163 are read from the second pixel 162. In the second pixel 162, the photodiode 164 is used for the AEC and does not contribute to the creation of an X-ray image. Accordingly, when the aperture areas of the photodiodes 163 and 164 are the same, the amount of accumulated charges is substantially a half of the amount of charges accumulated in the first pixel 161 with the same incident dose, but the degradation in image quality of an X-ray image is suppressed, compared with the above-mentioned embodiment in which the pixel value cannot be obtained from the place of the detection pixel 65 and thus the defect correction has to be performed. When a coefficient or the like to be multiplied by the pixel value of the second pixel 162 and corresponding to the pixel value of the first pixel 161 is calculated in advance on the basis of the aperture areas of the photodiodes 163 and 164 and the coefficient is multiplied by the output of the second pixel 162 to correct the output, it is possible to generate an X-ray image without performing the defect correction and to almost completely exclude the adverse influence on the image quality of the X-ray image due to using some pixels of the FPD for the AEC.

In the above-mentioned embodiments, it is stated that the electronic cassette 13 and the radiography platform 15 are formed as individual members, but a radiography platform having the FPD mounted thereon may be used. It is also stated that the console 14 and the electronic cassette 13 are separated components. However, the console 14 does not need to be an independent apparatus, and the functions of the console 14 may be mounted on the electronic cassette 13. The source controller 11 and the console 14 may be formed as a unified member. The present invention can be applied to an X-ray image detector which is fixed to a radiography platform, as well as the electronic cassette which is the portable X-ray image detector.

The present invention can be applied to a radiographic system using other radiation such as γ-rays other than X-rays.

What is claimed is:
1. A radiographic system comprising:
   a radiation source that irradiates a subject with radiation from different directions at a plurality of irradiation positions;
   a radiological image detector that includes a detection panel in which a plurality of pixels receiving radiation passing through the subject are arranged, and that receives the radiation radiated from a plurality of irra- diation directions from the radiation source and detects a series of radiological images;

a plurality of dose sensors that are arranged on an imaging plane on which the pixels of the detection panel are formed and that detect the dose of radiation passing through the subject;

a detection field setting unit that sets a detection field of the dose sensors, which is used to detect the dose of radiation passing through the subject, depending on the irradiation positions of the radiation source;

a density adjusting unit that adjusts the densities of the detection fields of the series of radiological images on the basis of the dose detected by the dose sensors in the detection field; and a tomographic image generating unit that generates a tomographic image of the subject from the series of radiological images.

2. The radiographic system according to claim 1, wherein the detection field setting unit sets the detection field, on the basis of the position and size of a region of interest of the subject and a movement position of the radiation source.

3. The radiographic system according to claim 2, further comprising a region of interest setting unit that sets the position and size of a region of interest of the subject.

4. The radiographic system according to claim 2, wherein the density adjusting unit compares the integrated value of the doses detected by the dose sensors in the detection field with a predetermined irradiation stop threshold, and performs an automatic exposure control of stopping the irradiation with radiation from the radiation source when the integrated value reaches the irradiation stop threshold.

5. The radiographic system according to claim 2, wherein the density adjusting unit adjusts a gain of image data of the radiological image on the basis of the integrated value of the doses detected by the dose sensors in the detection field when reading the image data from the detection panel.

6. The radiographic system according to claim 3, wherein the detection field setting unit calculates a distance X1 from the radiation source to an edge of the detection field close to the radiation source, and a distance X2 from the radiation source to an edge of the detection field distant from the radiation source through the use of the following expressions (1) and (2):

$$X1 = SID/(SID - H_{ROI}) \times (L_{XRAI} - L_{ROI}/2) \quad (1)$$

$$X2 = SID/(SID - H_{ROI}) \times (L_{XRAI} + L_{ROI}/2) \quad (2)$$

where $L_{ROI}$ represents the size of the region of interest in the moving direction of the radiation source, SID represents the distance between the detection panel and the radiation source in the direction perpendicular to the imaging plane of the detection panel, $L_{XRAI}$ represents position information of the moving direction of the radiation source with respect to the central axis of the region of interest in the direction perpendicular to the imaging plane of the detection panel, and $H_{ROI}$ represents the distance from the imaging plane of the detection panel to the region of interest.

7. The radiographic system according to claim 3, wherein the density adjusting unit compares the integrated value of the doses detected by the dose sensors in the detection field with a predetermined irradiation stop threshold, and performs an automatic exposure control of stopping the irradiation with radiation from the radiation source when the integrated value reaches the irradiation stop threshold.

8. The radiographic system according to claim 3, wherein the density adjusting unit adjusts a gain of image data of the radiological image on the basis of the integrated value of the doses detected by the dose sensors in the detection field when reading the image data from the detection panel.

9. The radiographic system according to claim 6, wherein the density adjusting unit compares the integrated value of the doses detected by the dose sensors in the detection field with a predetermined irradiation stop threshold, and performs an automatic exposure control of stopping the irradiation with radiation from the radiation source when the integrated value reaches the irradiation stop threshold.

10. The radiographic system according to claim 6, wherein the density adjusting unit adjusts a gain of image data of the radiological image on the basis of the integrated value of the doses detected by the dose sensors in the detection field when reading the image data from the detection panel.

11. The radiographic system according to claim 1, wherein the detection field setting unit sets the detection field on the basis of an irradiation field of the radiation radiated from the radiation source and the movement position of the radiation source.

12. The radiographic system according to claim 11, wherein the radiation source further includes an irradiation field limiter that sets the irradiation field.

13. The radiographic system according to claim 12, wherein the detection field setting unit calculates a distance X1a from the radiation source to an edge of the detection field close to the radiation source, and a distance X2a from the radiation source to an edge of the detection field distant from the radiation source through the use of the following expressions (3) and (4):

$$X1a = SID \cdot \tan(\theta 1 - \theta 2/2) \quad (3)$$

$$X2a = SID \cdot \tan(\theta 1 + \theta 2/2) \quad (4)$$

where L1 represents position information of the moving direction of the radiation source with respect to the central position of the imaging plane of the detection panel, $\theta 1$ represents the irradiation angle of radiation with respect to the imaging plane of the detection panel, and $\theta 2$ represents the opening angle of the irradiation field limiter.

14. The radiographic system according to claim 11, wherein the density adjusting unit compares the integrated value of the doses detected by the dose sensors in the detection field with a predetermined irradiation stop threshold, and performs an automatic exposure control of stopping the irradiation with radiation from the radiation source when the integrated value reaches the irradiation stop threshold.

15. The radiographic system according to claim 11, wherein the density adjusting unit adjusts a gain of image data of the radiological image on the basis of the integrated value of the doses detected by the dose sensors in the detection field when reading the image data from the detection panel.

16. The radiographic system according to claim 1, wherein the detection field setting unit specifies a region of interest of the subject from a firstly-detected radiological image out of the series of radiological images detected by the radiological image detector, and sets the detection field to be used to detect the second or subsequent radiological image on the basis of the detection field corresponding to the region of interest and the movement position of the radiation source.

17. The radiographic system according to claim 1, wherein the density adjusting unit compares the integrated value of the doses detected by the dose sensors in the detection field with a predetermined irradiation stop threshold, and performs an automatic exposure control of stopping the irradiation with radiation from the radiation source when the integrated value reaches the irradiation stop threshold.

18. The radiographic system according to claim 1, wherein the density adjusting unit adjusts a gain of image data of the radiological image on the basis of the integrated value of the doses detected by the dose sensors in the detection field when reading the image data from the detection panel.

19. The radiographic system according to claim 18, wherein the density adjusting unit normalizes the series of radiological images of which the gain is adjusted by multiplying the radiological images by the reciprocal of the gain.

20. A control method of a radiographic system according to claim 1, the control method comprising:
   setting a detection field, which is used to detect the dose of radiation passing through the subject, from a plurality of dose sensors arranged on an imaging plane of the detection panel on which the pixels are formed depending on the irradiation position of the radiation source;
   adjusting the densities of the detection fields of the series of radiological images on the basis of the dose detected by the dose sensors in the detection field; and
   generating a tomographic image of the subject from the series of radiological images.

* * * * *